(12) United States Patent
O'Shaughnessy et al.

(10) Patent No.: US 9,014,224 B2
(45) Date of Patent: Apr. 21, 2015

(54) COMPACT, THERMALLY STABLE MULTI-LASER ENGINE

(75) Inventors: John O'Shaughnessy, Carlsbad, CA (US); David E. Hargis, San Diego, CA (US); Steven Lee Miller, Golden, CO (US); Mark Lin, Carlsbad, CA (US)

(73) Assignee: CVI Laser, LLC., Albuquerque, NM (US)

( * ) Notice: Subject to any disclaimer, the term of this patent is extended or adjusted under 35 U.S.C. 154(b) by 0 days.

(21) Appl. No.: 12/940,004

(22) Filed: Nov. 4, 2010

(65) Prior Publication Data

US 2011/0134949 A1    Jun. 9, 2011

Related U.S. Application Data

(63) Continuation-in-part of application No. 12/418,537, filed on Apr. 3, 2009, now Pat. No. 7,903,706.

(60) Provisional application No. 61/042,652, filed on Apr. 4, 2008.

(51) Int. Cl.
| | | |
|---|---|---|
| *H01S 3/04* | (2006.01) | |
| *H01S 3/23* | (2006.01) | |
| *G01N 21/25* | (2006.01) | |
| *G01N 21/03* | (2006.01) | |
| *G01N 21/05* | (2006.01) | |
| *H01S 3/00* | (2006.01) | |
| *H01S 3/02* | (2006.01) | |

(52) U.S. Cl.
CPC .......... *H01S 3/2383* (2013.01); *G01N 21/0332* (2013.01); *G01N 21/05* (2013.01); *G01N 21/255* (2013.01); *H01S 3/005* (2013.01); *H01S 3/025* (2013.01); *H01S 3/027* (2013.01); *H01S 3/2391* (2013.01); *G01N 2021/0346* (2013.01)

(58) Field of Classification Search
USPC .................................. 372/23, 34, 36, 50.121
See application file for complete search history.

(56) References Cited

U.S. PATENT DOCUMENTS

| | | |
|---|---|---|
| 4,296,995 A | 10/1981 | Bickel |
| 4,550,240 A | 10/1985 | Toida et al. |
| 4,573,465 A | 3/1986 | Sugiyama et al. |
| 4,632,554 A | 12/1986 | Pearce |

(Continued)

FOREIGN PATENT DOCUMENTS

| | | |
|---|---|---|
| DE | 41 13 279 | 10/1992 |
| DE | 195 08 754 | 6/1999 |

(Continued)

OTHER PUBLICATIONS

Olympus Confocal Laser Scanning Biological Microscope, FV1000, Fluoview—Always Evolving, available at http://www.olympusamerica.com/files/seg_bio/fv1000_brochure.pdf.

*Primary Examiner* — Xinning Niu
(74) *Attorney, Agent, or Firm* — Knobbe Martens Olson & Bear LLP

(57) ABSTRACT

Various embodiments of a multi-laser system are disclosed. In some embodiments, the multi-laser system includes a plurality of lasers, a plurality of laser beams, a beam positioning system, a thermally stable enclosure, and a temperature controller. The thermally stable enclosure is substantially made of a material with high thermal conductivity such as at least 5 W/(m K). The thermally stable enclosure can help maintain alignment of the laser beams to a target object over a range of ambient temperatures.

57 Claims, 22 Drawing Sheets

(56) References Cited

U.S. PATENT DOCUMENTS

| | | | |
|---|---|---|---|
| 4,722,591 A | 2/1988 | Haffner | |
| 4,817,101 A | 3/1989 | Wyeth et al. | |
| 4,938,593 A | 7/1990 | Morris et al. | |
| 4,983,042 A * | 1/1991 | Korner et al. | 356/511 |
| 5,106,192 A | 4/1992 | Tucker et al. | |
| 5,109,447 A | 4/1992 | Can | |
| 5,147,349 A | 9/1992 | Johnson et al. | |
| 5,152,759 A | 10/1992 | Parel et al. | |
| 5,258,989 A | 11/1993 | Raven | |
| 5,260,578 A | 11/1993 | Bliton et al. | |
| 5,289,557 A | 2/1994 | Sheinis et al. | |
| 5,295,143 A | 3/1994 | Rao et al. | |
| 5,304,167 A | 4/1994 | Freiberg | |
| 5,325,393 A | 6/1994 | Nighan, Jr. et al. | |
| 5,343,038 A | 8/1994 | Nishiwaki et al. | |
| 5,394,492 A | 2/1995 | Hwang | |
| 5,446,532 A * | 8/1995 | Yamazaki | 356/73 |
| 5,491,344 A | 2/1996 | Kenny et al. | |
| 5,544,271 A | 8/1996 | Lim | |
| 5,617,500 A | 4/1997 | Shionoya et al. | |
| 5,633,695 A | 5/1997 | Feke et al. | |
| 5,659,642 A | 8/1997 | King et al. | |
| 5,668,903 A | 9/1997 | Neuberger et al. | |
| 5,674,698 A | 10/1997 | Zarling et al. | |
| 5,698,397 A | 12/1997 | Zarling et al. | |
| 5,736,410 A | 4/1998 | Zarling et al. | |
| 5,771,325 A | 6/1998 | Neuberger | |
| 5,814,820 A | 9/1998 | Dong et al. | |
| 5,823,942 A | 10/1998 | Toida | |
| 5,824,269 A * | 10/1998 | Kosaka et al. | 422/73 |
| 5,866,911 A | 2/1999 | Baer | |
| 5,952,668 A | 9/1999 | Baer | |
| 6,048,444 A | 4/2000 | Takahashi et al. | |
| 6,081,544 A * | 6/2000 | Zamel et al. | 372/107 |
| 6,101,201 A | 8/2000 | Hargis et al. | |
| 6,110,165 A | 8/2000 | Ota | |
| 6,133,995 A | 10/2000 | Kubota | |
| 6,175,440 B1 * | 1/2001 | Conemac | 359/204.1 |
| 6,214,033 B1 | 4/2001 | Li et al. | |
| 6,215,807 B1 | 4/2001 | Reilly | |
| 6,221,671 B1 | 4/2001 | Groner et al. | |
| 6,222,961 B1 | 4/2001 | Engelhardt et al. | |
| 6,462,345 B1 | 10/2002 | Simon et al. | |
| 6,480,513 B1 | 11/2002 | Kapany et al. | |
| 6,490,309 B1 | 12/2002 | Okazaki et al. | |
| 6,510,001 B1 | 1/2003 | Engelhardt et al. | |
| 6,557,369 B1 | 5/2003 | Phelps et al. | |
| 6,592,822 B1 | 7/2003 | Chandler | |
| 6,603,780 B2 * | 8/2003 | Miyai | 372/23 |
| 6,614,031 B2 | 9/2003 | Engelhardt et al. | |
| 6,654,165 B2 | 11/2003 | Engelhardt et al. | |
| 6,677,566 B2 | 1/2004 | Knebel et al. | |
| 6,737,635 B2 | 5/2004 | Engelhardt et al. | |
| 6,750,457 B2 | 6/2004 | Heffelfinger et al. | |
| 6,836,489 B2 | 12/2004 | Nishimura et al. | |
| 6,867,899 B2 | 3/2005 | Knebel | |
| 6,867,919 B2 | 3/2005 | Seyfried | |
| 6,920,159 B2 | 7/2005 | Sidorin et al. | |
| 6,958,470 B2 | 10/2005 | Hoffmann | |
| 6,980,293 B1 | 12/2005 | Harada | |
| 7,005,654 B2 | 2/2006 | Seyfried | |
| 7,098,447 B2 | 8/2006 | Moellmann | |
| 7,133,130 B2 | 11/2006 | Storz et al. | |
| 7,151,633 B2 | 12/2006 | Storz et al. | |
| 7,280,567 B2 | 10/2007 | Luo et al. | |
| 7,280,570 B2 | 10/2007 | Seyfried et al. | |
| 7,330,493 B2 | 2/2008 | Luo et al. | |
| 7,394,063 B2 | 7/2008 | Schreiber | |
| 7,426,027 B2 | 9/2008 | Noguchi et al. | |
| 7,428,104 B2 | 9/2008 | Engelhardt | |
| 7,430,231 B2 | 9/2008 | Luo et al. | |
| 7,433,119 B2 | 10/2008 | Gugel | |
| 7,457,330 B2 | 11/2008 | Luo et al. | |
| 7,468,998 B2 | 12/2008 | Luo et al. | |
| 7,474,462 B2 | 1/2009 | Ulrich et al. | |
| 7,505,495 B2 | 3/2009 | Fratti et al. | |
| 7,522,651 B2 | 4/2009 | Luo et al. | |
| 7,535,937 B2 | 5/2009 | Luo et al. | |
| 7,535,938 B2 | 5/2009 | Luo et al. | |
| 7,542,489 B2 | 6/2009 | Luo et al. | |
| 7,548,567 B2 | 6/2009 | Kupershmidt et al. | |
| 7,564,624 B2 | 7/2009 | Leimbach et al. | |
| 7,599,115 B2 | 10/2009 | Gugel | |
| 7,599,413 B2 | 10/2009 | Luo et al. | |
| 7,606,273 B2 | 10/2009 | Zhu et al. | |
| 7,633,979 B2 | 12/2009 | Luo et al. | |
| 7,660,035 B2 | 2/2010 | Bohm et al. | |
| 7,724,363 B2 | 5/2010 | Wachsmuth et al. | |
| 7,733,932 B2 * | 6/2010 | Faybishenko | 372/36 |
| 7,742,226 B2 | 6/2010 | Bewersdorf et al. | |
| 7,813,390 B2 | 10/2010 | Luo et al. | |
| 7,835,601 B2 | 11/2010 | Seyfried et al. | |
| 7,899,105 B1 | 3/2011 | Hargis et al. | |
| 7,903,706 B2 | 3/2011 | O'Shaughnessy et al. | |
| 7,949,025 B2 | 5/2011 | Olea | |
| 7,999,935 B2 | 8/2011 | Dyba | |
| 8,238,389 B2 | 8/2012 | Hargis et al. | |
| 2001/0017868 A1 | 8/2001 | Kraenert et al. | |
| 2001/0021210 A1 | 9/2001 | Nakaya et al. | |
| 2002/0061032 A1 | 5/2002 | Miura et al. | |
| 2002/0097772 A1 | 7/2002 | Dautremont-Smith et al. | |
| 2003/0058530 A1 | 3/2003 | Kawano | |
| 2003/0214987 A1 * | 11/2003 | Yamanaka et al. | 372/43 |
| 2004/0027631 A1 | 2/2004 | Nagano et al. | |
| 2004/0210289 A1 | 10/2004 | Wang et al. | |
| 2005/0180474 A1 | 8/2005 | Buchold et al. | |
| 2005/0201441 A1 | 9/2005 | Seyfried et al. | |
| 2005/0220458 A1 | 10/2005 | Kupershmidt et al. | |
| 2005/0281298 A1 | 12/2005 | Kupershmidt et al. | |
| 2006/0097188 A1 | 5/2006 | Seyfried | |
| 2006/0239317 A1 | 10/2006 | Yoshida et al. | |
| 2006/0245049 A1 | 11/2006 | Knebel | |
| 2006/0273260 A1 | 12/2006 | Casstevens et al. | |
| 2007/0024978 A1 * | 2/2007 | Jackson et al. | 359/569 |
| 2008/0025677 A1 * | 1/2008 | Sasaki | 385/94 |
| 2008/0089369 A1 | 4/2008 | Luo et al. | |
| 2009/0097507 A1 | 4/2009 | Zhu et al. | |
| 2009/0257054 A1 | 10/2009 | Hargis et al. | |
| 2009/0274176 A1 | 11/2009 | O'Shaughnessy et al. | |
| 2009/0323203 A1 * | 12/2009 | Adams et al. | 359/737 |
| 2010/0006772 A1 | 1/2010 | Gugel | |
| 2010/0073757 A1 | 3/2010 | Birk et al. | |
| 2010/0111768 A1 * | 5/2010 | Banerjee et al. | 422/82.08 |
| 2010/0177375 A1 | 7/2010 | Seyfried | |
| 2010/0232011 A1 | 9/2010 | Seyfried | |
| 2011/0222054 A1 | 9/2011 | Krishnamachari | |
| 2011/0273768 A1 | 11/2011 | Krishnamachari et al. | |

FOREIGN PATENT DOCUMENTS

| | | |
|---|---|---|
| JP | 07 318810 | 12/1995 |
| WO | WO 2010065779 | 6/2010 |

* cited by examiner

COMPACT, THERMALLY STABLE MULTI-LASER ENGINE

RELATED APPLICATIONS

This application is a continuation-in-part of U.S. patent application Ser. No. 12/418,537, filed Apr. 3, 2009 and titled "Compact, Thermally Stable Multi-Laser Engine", which claims the benefit of U.S. Provisional Application No. 61/042,652, filed Apr. 4, 2008, each of which is incorporated herein by reference in its entirety.

BACKGROUND

1. Field

This disclosure generally relates to optical (e.g., fluorescent, spectroscopic) analysis of biological samples through flow cells and/or optical fibers connected to confocal microscopes or "lab-on-a-chip" devices, and to, for example, compact, thermally stable multi-laser systems configured to couple to flow cells, optical fibers, or other target objects and to provide illumination thereto.

2. Description of Related Art

Optical analysis of flow cells, such as laser-induced fluorescence, involves illuminating biological samples with laser light in order to test samples which may, for example, be tagged with fluorescent dyes. Fluorescent dyes absorb light at certain wavelengths and in turn emit their fluorescence energy at a different wavelength. This emission can be detected to ascertain properties of the fluid in the flow cell. Existing systems for fluorescent analysis of flow cells, however, suffer from various drawbacks, such as measurement error.

SUMMARY

Embodiments described herein have several features, no single one of which is solely responsible for their desirable attributes. Without limiting the scope of the invention as expressed by the claims, some of the advantageous features will now be discussed briefly.

Various embodiments described herein provide the ability to perform optical measurements on flow cells while addressing some of the drawbacks encountered with conventional approaches, such as laser beam alignment to the flow cell that is sensitive to the ambient temperature resulting in signal power fluctuations.

A wide range of embodiments are disclosed. Some embodiments, for example, comprise a compact, thermally stable multi-laser system. The multi-laser system comprises a plurality of lasers. The plurality of lasers outputs a plurality of respective laser beams. The system further comprises a beam positioning system. The beam positioning system is configured to position the plurality of laser beams closer together. The multi-laser system further comprises beam focusing optics. The beam focusing optics are configured to focus the plurality of laser beams. The multi-laser system further comprises a thermally stable enclosure. The thermally stable enclosure encloses the plurality of lasers, the beam positioning system and the beam focusing optics. The thermally stable enclosure is configured to thermally and mechanically couple to a flow cell. The thermally stable enclosure substantially comprises a material with high thermal conductivity of at least 5 W/(m K). The thermally stable enclosure has a volume of no more than 36 cubic inches. The system further comprises a temperature controller. The temperature controller is configured to control the temperature of the thermally stable enclosure and to maintain the alignment of the focused laser beams to the flow cell over a range of ambient temperatures.

In some embodiments, a compact, thermally stable multi-laser system comprises a plurality of lasers. The plurality of lasers outputs a plurality of respective laser beams. The system further comprises a beam positioning system. The beam positioning system is configured to reposition the plurality of laser beams. The system further comprises a thermally stable enclosure. The thermally stable enclosure encloses the plurality of lasers and the beam positioning system. The thermally stable enclosure substantially comprises a material with high thermal conductivity of at least 5 W/(m K). The thermally stable enclosure is configured to control the temperature of the thermally stable enclosure and configured to maintain the alignment of the focused laser beams to a target object over a range of ambient temperatures. The system further comprises a temperature controller. The temperature controller is configured to control the temperature of the thermally stable enclosure. Other embodiments are also disclosed.

BRIEF DESCRIPTION OF THE DRAWINGS

The following drawings and the associated descriptions are provided to illustrate embodiments of the present disclosure and do not limit the scope of the claims.

DETAILED DESCRIPTION

Although certain preferred embodiments and examples are disclosed herein, inventive subject matter extends beyond the specifically disclosed embodiments to other alternative embodiments and/or uses of the inventions, and to modifications and equivalents thereof. Thus, the scope of the inventions herein disclosed is not limited by any of the particular embodiments described below. For example, in any method or process disclosed herein, the acts or operations of the method or process may be performed in any suitable sequence and are not necessarily limited to any particular disclosed sequence.

For purposes of contrasting various embodiments with the prior art, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 1:
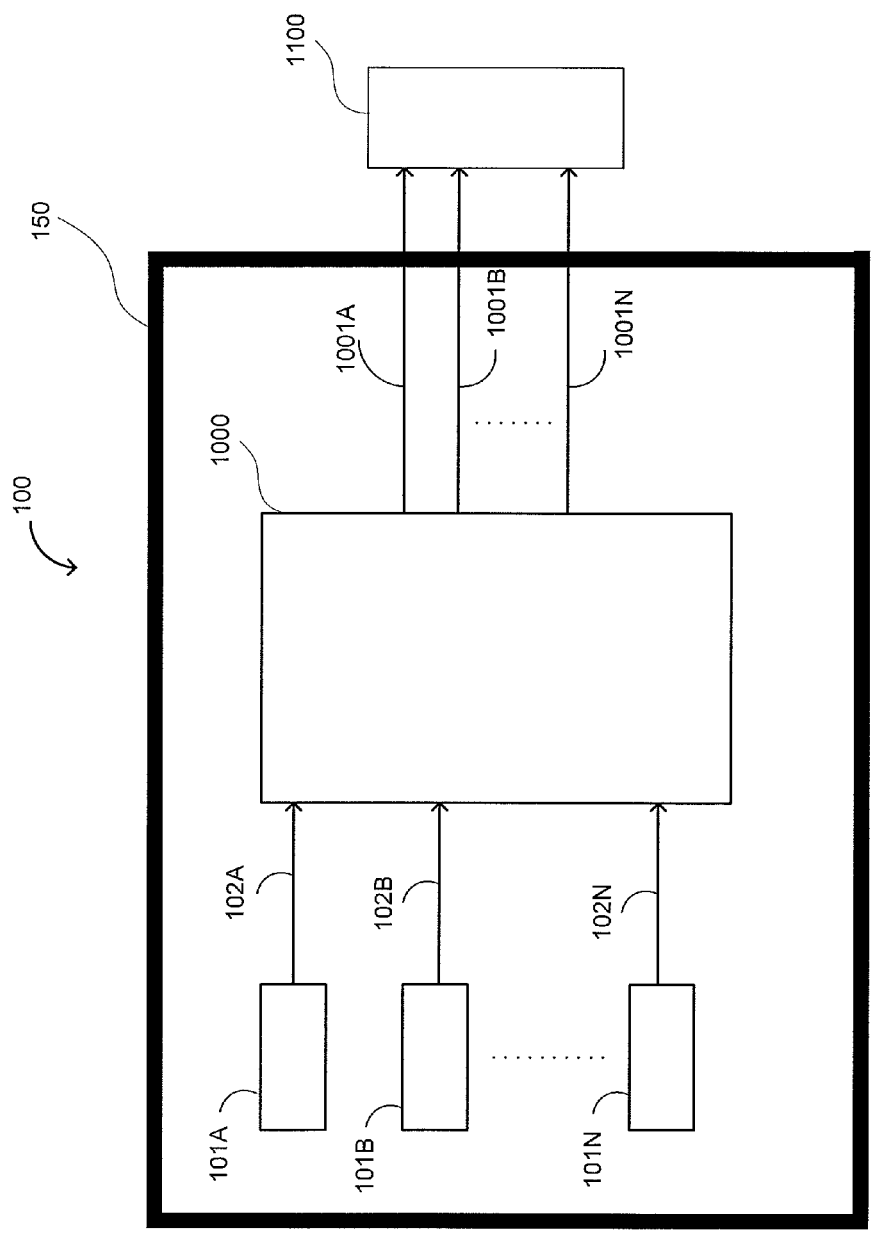
FIG. 1 depicts an example embodiment of a multi-laser system.

FIG. 1 depicts an example embodiment of a multi-laser system. The multi-laser system 100 depicted in FIG. 1 comprises a thermally stable, temperature controlled enclosure 150 configured to mechanically and/or thermally couple to a target object 1100. The enclosure 150 helps to isolate the laser and optics within the enclosure 150 from the ambient environment, which may have varying temperature. By maintaining the temperature within the enclosure within a relatively small range, thermally induced laser wavelength and intensity fluctuations as well as pointing instabilities of the laser beams can be reduced or minimized. In some embodiments, the target object may comprise a flow cell, a flow cell mount, a light pipe, a waveguide, an optical fiber, or a lab on a chip. In some embodiments, the target object may comprise a mounting mechanism, mounting system (e.g., mounting alignment system), etc. for a flow cell, a flow cell mount, a light pipe, a waveguide, an optical fiber, and/or a lab on a chip.

In some embodiments, the temperature across the enclosure may be stable over time and with changes in the ambient temperature. The constant temperature over time may help with long term system performance. For example if the enclosure temperature were to change with time, then the system performance would also potentially degrade with time. This could eventually result in servicing the system, e.g., to realign the system.

The thermally stable enclosure 150 comprises a material with high thermal conductivity. In some embodiments, a material with thermal conductivity of at least about 5 W/(m K), (e.g., between about 5 W/(m K) and about 2000 W/(m K)) is used. In some embodiments, a material with thermal conductivity at least about 50 W/(m K) (e.g., between about 50 W/(m K) and about 2000 W/(m K)) is used. In other embodiments, a material with thermal conductivity of about 375 W/(m K) or greater is used. In other embodiments, a material with thermal conductivity of at least about 380 W/(m K) is used. In some embodiments, a material with thermal conductivity between about 125 W/(m K) and about 425 W/(m K)) is used. In some embodiments, a material with thermal conductivity between about 375 W/(m K) and about 425 W/(m K)) is used. In some embodiments, a material with thermal conductivity between about 125 W/(m K) and about 250 W/(m K)) is used. In some embodiments, a material with thermal conductivity between about 200 W/(m K) and about 250 W/(m K)) is used. In some embodiments, the material has a heat capacity corresponding o the heat capacity of the materials described herein. The use of such thermally conductive material helps ensure a relatively reduced temperature variation within the enclosure 150, even when the ambient temperature outside of the enclosure varies relatively widely.

As described more fully below, a temperature controller in thermal contact with the enclosure adjusts the temperature of the enclosure in response to variations in ambient conditions. A highly thermally conductive enclosure enables the temperature controller to more quickly and effectively maintain the enclosure and system temperature without temperature gradients in response to such variations in ambient conditions. A variety of thermally conductive materials can be used (e.g., copper, aluminum, copper tungsten, ceramics, epoxy, etc.). In some embodiments, a material with a thermal conductivity of at least 5 W/(m K) may be used. In other embodiments, a material with a thermal conductivity of less than 5 W/(m K) may be used. The thermally conductive material can be used to form the entire enclosure, or merely a portion thereof. In certain embodiments, the enclosure substantially comprises highly thermally conductive material. For example, highly thermally conductive material can be used to form the top, the bottom, or any number of the sides of the enclosure 150, or any combination thereof. In some embodiments, a majority of the enclosure 150 is made of the substantially thermally conductive material. In some embodiments, only a relatively small portion of the enclosure 150 is made of the thermally conductive material. In some embodiments, a substantial portion of the enclosure 150 is made of the substantially thermally conductive material. In some embodiments, multiple substantially thermally conductive materials can be used, with some areas of the enclosure 150 being more thermally conductive than others.

The multi-laser system 100 includes a plurality of lasers 101A-101N, enclosed within the thermally stable enclosure 150. The plurality of lasers 101A-101N may comprise diode lasers, solid-state lasers, frequency-doubled lasers, and/or other types of lasers. The plurality of lasers 101A-101N output a plurality of respective laser beams 102A-102N. Each of the laser beams 102A-102N may have a wavelength different from the other laser beams.

As shown in FIG. 1, the multi-laser system 100 further includes a beam positioning system 1000. To achieve a desired spatial arrangement of the laser beams 102A-102N, the inherent laser beam boresight and centration errors present in lasers 101A-101N, as well angular and lateral positioning errors present in the multi-laser system's optomechanical components can be compensated for. In some embodiments, the beam positioning/combining system 1000 may include mechanical and/or opto-mechanical provisions to perform such compensation.

Mechanical provisions to the laser mounting may be used to adjust the angular and/or lateral position of the lasers so that the boresight and centration errors of the lasers 101A-101N as well as the angular and lateral positioning errors of the opto-mechanical components are compensated for. The aligned laser beams may then be positioned or combined by the beam positioning/combining system 1000 into a desired spatial arrangement that a specific application requires.

Opto-mechanical provisions to the beam positioning/ alignment system may be used to allow for angular and lateral position adjustment of the laser beams. This adjustment capability may help compensate for the lasers' boresight and centration errors as well as the angular and lateral positioning errors of the opto-mechanical components to achieve a desired spatial arrangement of the laser beams.

In embodiments in which the system is used perform testing of biological samples, flow cells are illuminated with laser beams. Fluorescent dyes absorb light at certain wavelengths and in turn emit their fluorescence energy at a different wavelength. This emission can be detected to ascertain properties of the fluid in the flow cell. Temperature variations may cause the wavelength and/or the intensity of light output by the lasers to vary. Such variations in the laser beams directed into the flow cell may cause fluctuations in output fluorescent signals, which may introduce inaccuracy in the optical measurements. Temperature variations and/or temperature gradients also may cause movement of the optical elements (e.g., due to thermal expansion) and resultant shifting of the laser beams. These pointing errors may cause the laser beams to deviate from the flow cell, such that the signal changes, or is altogether lost, again introducing inaccuracy in the test results.

Temperature variations can result from ambient temperature fluctuations. Accordingly, reducing the temperature variation of and the presence of temperature gradients within the laser beam system can improve the accuracy and usability of the test results.

Figure 2:
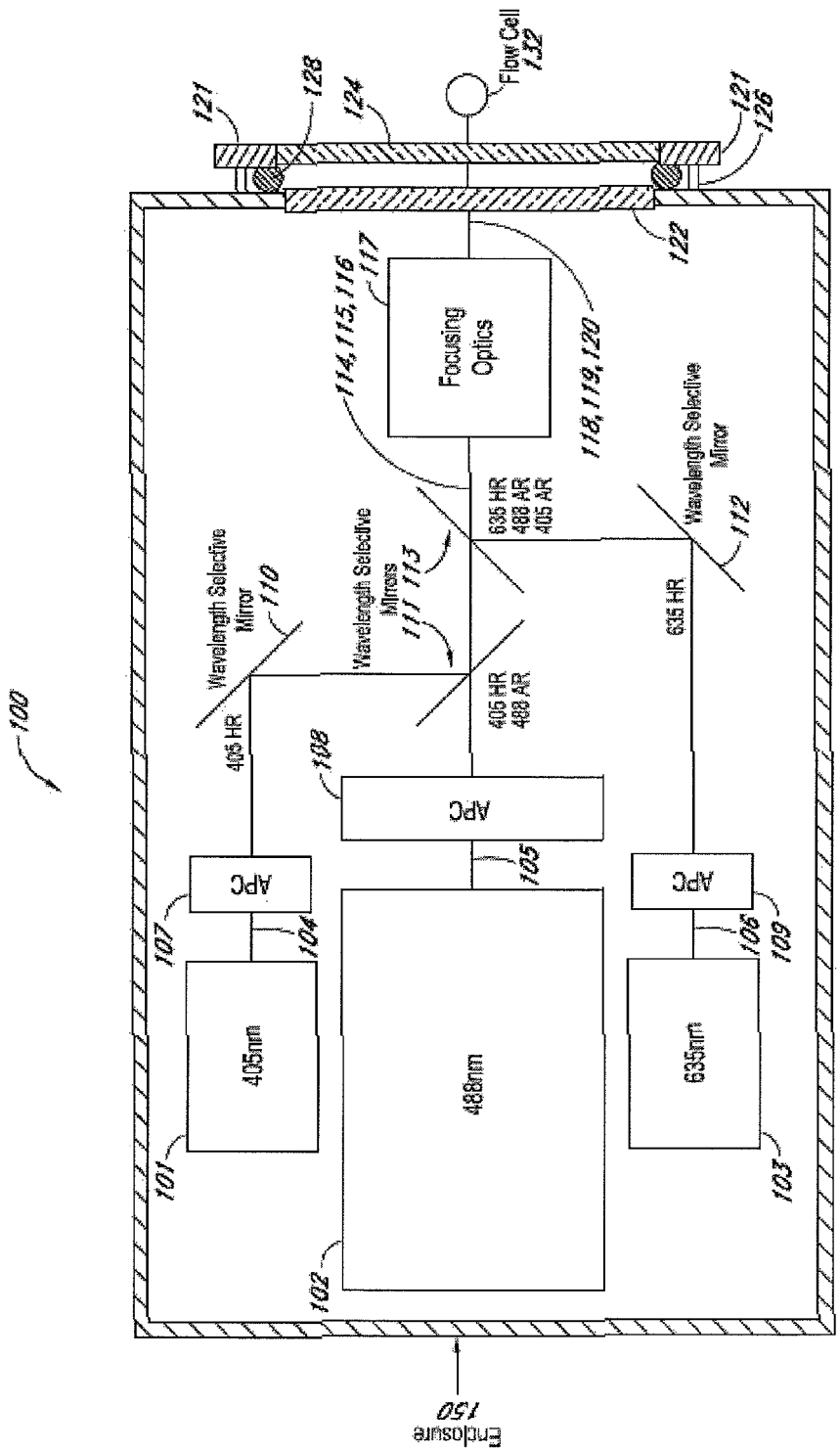
FIG. 2 depicts another example embodiment of a multi-laser system.

Various embodiments described herein may address one or more of these problems. FIG. 2 is a top view of another example embodiment of the multi-laser system 100. The multi-laser system 100 depicted in FIG. 2 comprises a thermally stable enclosure 150 configured to mechanically and/or thermally couple to a flow cell 132. The thermally stable enclosure 150 helps to isolate the laser and optics within the enclosure 150 from the ambient environment, which may have varying temperature. In some embodiments, the enclosure 150 can achieve thermal stability through the use of a temperature controller, as discussed in relation to FIG. 3 below. In various embodiments, the enclosure 150 helps reduce variations in the temperature of the various components of the multi-laser system 100. By maintaining the temperature within the enclosure within a relatively small range, thermally induced laser wavelength and intensity fluctuations as well as pointing instabilities of the laser beams can be reduced or minimized and alignment of the laser beams to a target object may be maintained over a range of ambient temperatures (e.g., between about 10° C. and about 55° C.). Accordingly, the use of a thermally stable enclosure 150 may help achieve more accurate test results.

Some materials expand and contract when heated or cooled. Changes in the enclosure temperature or temperature variations across the enclosure can result in a change in the relative positions of lasers, mirrors, lenses, and the target object (e.g., flow cell). Some lasers exhibit beam pointing that is temperature dependent. This may be due in part to the fact that different materials are used in the construction of the laser (e.g., metals, glass, adhesives, etc). The different materials may have different thermal expansion coefficients, which may cause beam deviations when the laser system's temperature changes. Some mirror and lens systems also show some temperature dependence for the same reason.

The multi-laser system 100 depicted in FIG. 2 includes a plurality of lasers 101, 102, 103 enclosed within the thermally stable enclosure 150. Although FIG. 2 includes three lasers, a different number of lasers can be used. The multi-laser system 100 shown in FIG. 2 includes a 405 nm laser, a 488 nm laser and a 635 nm laser, but other wavelengths can also be used (e.g., lasers having wavelengths of 375 nm, 440 nm, 515 nm, 561 nm, 594 nm, 640 nm, etc.).

The plurality of lasers 101, 102, 103 output a plurality of respective laser beams 104, 105, 106. Laser beam 104 has a first wavelength, laser beam 105 has a second wavelength, and laser beam 106 has a third wavelength. The first, second, and third wavelengths are different from one another. In FIG. 2, these wavelengths are 405 nm, 488 nm and 635 nm, respectively, but other wavelengths can also be used (e.g., 375 nm, 440 nm, 515 nm, 561 nm, 594 nm, 640 nm, etc.).

As shown in the example embodiment of FIG. 2, the multi-laser system 100 further includes a plurality of automatic power control (APC) modules 107, 108, 109. In some embodiments, the APC modules 107, 108, 109 may each comprise a beamsplitter (not shown) and a photodetector (not shown) configured to sample light from the laser beams 104, 105, 106, respectively, and to feed back the signal from the detector in communication with a laser controller (not shown) to adjust the output power of lasers 101, 102, 103, respectively. Other approaches may also be possible.

Referring still to FIG. 2, the beam positioning system comprises a plurality of wavelength selective mirrors 110, 111, 112, 113. In various embodiments, some of the wavelength selective 110, 111, 112, 113 mirrors have significantly different reflection or transmission properties at different wavelengths. Accordingly, the wavelength selective mirrors 110, 111, 112, 113 can separate or combine laser beams with different wavelengths. In some embodiments, the mirrors 110, 112 may be broadband, for example because light is not transmitted through the mirrors 110, 112. Through the use of suitable optical coatings, wavelength selective mirrors exhibit high reflection over some range of wavelengths and high transmission over another range of wavelengths. The wavelength selective mirrors are appropriate for the wavelengths of the laser sources. For example, various of the wavelength selective mirrors will selectively reflect (or transmit) light propagating from one laser at a first wavelength and not light propagating from another laser at a second wavelength. The example embodiment of FIG. 2 depicts four wavelength selective mirrors 110, 111, 112, 113. In other embodiments, a different number of wavelength selective mirrors may be used (e.g., see FIG. 2A). In some embodiments, the wavelength selective mirrors may comprise dichroic and trichroic mirrors. Dichroic mirrors can separate or combine lasers with two different wavelengths. In various embodiments dichroic mirrors may allow at least one wavelength to substantially or totally pass through and may substantially or totally reflect at least one wavelength. Trichroic mirrors can separate or combine lasers with three different wavelengths. Trichroic mirrors may be optimized for three wavelengths, they may have three peaks or one broad peak that covers multiple wavelengths. In other embodiments, the wavelength selective mirrors may comprise mirrors with selectivity for a different number of wavelengths. Alternatively, substantially non-wavelength selective mirrors that do not selectively reflect (or transmit) light of one laser and not light of another laser may be inserted in the path of the beam to redirect and/or alter the beam path or the beam. Other optical elements can be inserted into the optical path.

The wavelength selective mirrors 110, 111, 112, 113 are configured with highly reflective and anti-reflective coatings in accordance with the wavelengths of the plurality of laser beams 104, 105, 106. As shown in FIG. 2, wavelength selective mirror 110 is configured to be highly reflective of the wavelength of the laser beam 104 (e.g., 405 nm, all wavelengths); wavelength selective mirror 111 is configured to be highly reflective of the wavelength of the laser beam 104 (e.g., 405 nm) and anti-reflective of the wavelength of the laser beam 105 (e.g., 488 nm); wavelength selective mirror 112 is configured to be highly reflective of the wavelength of the laser beam 106 (e.g., 635 nm, all wavelengths), and wavelength selective mirror 113 is configured to be highly reflective of the wavelength of the laser beam 106 (e.g., 635 nm), and anti-reflective of the wavelengths of the laser beams 104 (e.g., 405 nm) and 105 (e.g., 488 nm). In other embodiments, the wavelength selective mirrors can be configured to be highly reflective of some wavelengths and anti-reflective of some other wavelengths in order to separate or combine the wavelengths as necessary.

In some embodiments, this plurality of wavelength selective mirrors 110, 111, 112, 113 may be supported by a plurality of respective flexure mounts (not shown). Flexure mounts are less likely to move with external vibrations and thus are less likely to require adjustment. Flexure mounts reduce impact on the optics from shocks such as may be introduced by shipping of the system. Additionally, flexure mounts typically exhibit less hysteresis than rolling or sliding contacts. Flexure mounts are typically fabricated from materials which make them relatively less sensitive to temperature variations. Flexure mounts may also be smaller than conventional spring loaded mounts. In some embodiments, the flexure mounts may comprise a nickel-iron alloy material for example. Other materials may also be used. In other embodiments, the plurality of wavelength selective mirrors 110, 111, 112, 113 may be supported by a plurality of respective spring-loaded mirror mounts (not shown). In other embodiments, the plurality of wavelength selective mirrors 110, 111, 112, 113 may be supported by a plurality of respective glue-block mounts (not shown).

In the multi-laser system 100 shown in FIG. 2, three optical paths are depicted. A first optical path at a wavelength of 405 nm originates at laser 101, passes through the APC 107, where a portion of the signal is picked off (e.g., by a beam splitter), is then highly reflected at wavelength selective mirrors 110 and 111 and transmitted through wavelength selective mirror 113, and then arrives at the focusing optics 117. A second optical path at a wavelength of 488 nm originates at laser 102, passes through the APC 108, where a portion of the signal is picked off (e.g., by a beam splitter), is then transmitted through wavelength selective mirrors 111 and 113, and then arrives at the focusing optics 117. A third optical path at a wavelength of 635 nm originates at laser 103, passes through the APC 109, where a portion of the signal is picked off (e.g., by a beam splitter), is then reflected at wavelength selective mirrors 112 and 113, and then arrives at the focusing optics 117. Propagating along these paths, laser beams 104, 105, 106, which may have originally been far from one another, are repositioned to be closer together as beams 114, 115, 116 and, after the focusing optics, beams 118, 119, 120, respectively. In some embodiments, the beams 118, 119, 120 are parallel to one another. In other embodiments, the beams 118, 119, 120 are not parallel to one another. Other mirrors and optical components (e.g., lenses, prisms, polarization rotators, waveplates, etc.) can be included to alter the laser beams and/or optical paths.

Still referring to FIG. 2, the multi-laser system 100 further includes optional beam focusing optics 117 to provide size reduction and/or shaping to the output laser beams 118, 119, 120. For example, the focusing optics 117 may focus a laser beam down to a smaller spot. Additionally, the focusing optics 117 may change the shape of the laser beams. In some embodiments, for example, the laser beams 118, 119, 120 can have a generally Gaussian profile, so that when illuminating a flow cell, the intensity of the light illuminating the center of the flow cell is significantly greater than the intensity of the light illuminating the peripheral edges of the flow cell. Accordingly, the beams of light 118, 119, 120 can be elongated (e.g., elliptical) beams, so that the relatively high intensity center regions of the light beams extend across the entire width of the flow cell, while the relatively low intensity outer regions of the light beams do not strike the flow cell. By using an elongated (e.g., elliptical) beam of light, a more uniform distribution of light across the width of the flow cell or other target output can be achieved while illuminating a relatively small longitudinal area along the length of the flow cell and maintaining substantially uniform high light intensity.

In some embodiments, the beams 114, 115, 116 enter the beam focusing optics 117 and can have circular cross-sections with a Gaussian fall-off. In some embodiments, the beam focusing optics 117 may include an anamorphic lens system which may produce non-rotationally symmetric or elongated beam such as a beam with elliptical cross-section and spot size. In other embodiments, the beam focusing optics 117 may include cylindrical lenses. In some embodiments, the beam focusing optics 117 may include spherical lenses. In some embodiment, the beam focusing optics 117 may include powell lenses (Gaussian to flat-top transformers). In some embodiments, the beam focusing optics 117 may include aspherical lenses. The focusing optics may be achromatic with reduced chromatic aberration thereby reducing positioning error which may otherwise result from different color laser beams. Accordingly, achromatic anamorphic optics, achromatic elliptical optics, achromatic spherical optics and achromatic aspherical optics, may be used. In some embodiments, lenses can be an anamorphic microlens array. In some embodiments, refractive and/or diffractive optics can be used to produce the elongated beams of light 118, 119, 120. Other types of optics are possible.

In cases where the laser comprises a semiconductor laser, the laser beam output may already be elliptical-shaped, and optics to convert the elliptical beam into a circular beam can be substantially excluded. In such cases, there would be no need to include anamorphic focusing optics to make the elliptical-shaped beam spherical (e.g., rotationally symmetric). Spherical or rotationally symmetric optics may be employed without anamorphic elements.

The output laser beams 118, 119 and 120 depicted in FIG. 2 may have respective spot sizes of between about 55 μm and about 110 μm in one direction and between about 5 μm and about 15 μm in another direction (e.g., perpendicular to the one direction). In other embodiments, the laser beams may have respective spot sizes of between about 70 μm and about 110 μm in one direction and between about 5 μm and about 15 μm in another direction (e.g., perpendicular to the one direction). In other embodiments, the laser beams may have respective spot sizes of between about 50 μm and about 150 μm in one direction and between about 5 μm and about 20 μm in another direction (e.g., perpendicular to the one direction). In other embodiments, the laser beams may have spot sizes of between about 55 μm and about 100 μm in one direction and between about 5 μm and about 15 μm in another direction (e.g., perpendicular to the one direction). In other embodiments, the laser beams may have spot sizes of between about 70 μm and about 100 μm in one direction and between about 5 μm and about 15 μm in another direction (e.g., perpendicular to the one direction). In other embodiments, the laser beams may have respective spot sizes of between about 50 μm and about 150 μm in one direction and between about 5 μm and about 20 μm in another direction (e.g., perpendicular to the one direction). In some embodiments, the output laser beams 118, 119, 120 may have respective spot sizes of about 80 μm in one direction and about 10 μm in another direction (e.g., perpendicular to the one direction). In other embodiments, the output laser beams 118, 119, 120 may have respective spot sizes of about 100 μm in one direction and about 10 μm in another direction (e.g., perpendicular to the one direction). The directions may correspond to major and minor axes of an ellipse for a beam with an elliptical cross-section and spot shape. Other sizes and shapes are possible for the light beams.

Still referring to FIG. 2, the multi-laser system 100 includes coupling to a flow cell 132. The multi-laser system 100 can include an output window 121 that allows the beams of light 118, 119, 120 to exit the enclosure 150. The output window 121 can be made from, for example, fused silica, glass, acrylic, or a variety of other transparent materials (e.g., plastic). In some embodiments, the enclosure 150 includes an aperture 122 in a wall thereof and the output window 121 comprises a transparent window pane 124 positioned over the aperture 122. The window pane 124 can be made from, for example, fused silica, glass, acrylic, or a variety of other transparent materials (e.g., plastic). The aperture 122 and window pane 124 can assume a variety of shapes, but in some embodiments they are rectangular, circular, or elliptical. The window 121 can be attached to the enclosure 150 by a plurality of fasteners such as bolts 126. In FIG. 2, only two bolts 126 are shown, but in some embodiments, additional bolts can be positioned along the edges of the window 121. In some embodiments, the window 121 can include a flange for mounting the window. The flange may have a plurality of through holes through which fasteners (e.g., bolts 126) can pass to secure the window 121 to the enclosure 150. A seal 128 (e.g., an O-ring) can be positioned between the enclosure 150 and the window 121. The bolts 126 can be tightened, causing the O-ring 128 to be compressed between the enclosure 150 and the window 121. In some embodiments, the O-ring 128 produces a hermetic seal. Other approaches can be used to fasten the window 121 to the enclosure 150. The window 121 can be secured to the enclosure 150 by an adhesive, epoxy, or cement.

In some embodiments, the seal described may produce a hermetic seal. A hermetic seal may help reduce particles and contamination from outside the enclosure. A hermetic seal may also help to prevent or reduce the flow of air currents and thus prevent or reduce the flow of ambient temperature changes into the enclosure. This in turn may help reduce temperature instability within the enclosure. In some of the embodiments discussed above, the entire enclosure 150 is hermetically sealed from the ambient air. Thus, the interior of the enclosure 150 is isolated from air currents which can cause temperature variation, and the internal optical elements are protected from external contaminants. In some embodiments a getter (not shown) is located inside the enclosure 150 which can reduce contaminant particles or chemical species. Additional, a desiccant (not shown) can be positioned inside the enclosure 150 to reduce moisture.

Although FIG. 2 shows a single output window, multiple output windows can be used. For example, each beam of light 118, 119, 120 can exit the enclosure 150 via a respective output window. In some embodiments, it is desirable that as much as possible of the enclosure 150 comprise the thermally conductive material, to better achieve temperature uniformity. Accordingly, the output windows can be separated by thermally conductive material and can cover only as much area as necessary to allow light beams 118, 119, 120 to leave the enclosure 150. However, in some embodiments, a single output window is easier and less expensive to construct.

The multi-laser system 100 can include a flow cell connector (not shown) that is mechanically and thermally coupled to the enclosure 150, and the flow cell connector is configured to secure a flow cell 132 so that it intersects and maintains the alignment of the beams of light 118, 119, 120. In some embodiments, the flow cell connector can permanently attach the flow cell 132 to the enclosure 150. However, in some embodiments, the flow cell connector can allow the flow cell 132 to be removably attached to the enclosure 150. In some embodiments, the flow cell connector can be compatible with multiple types and/or sizes of flow cells. For example, the flow cell connector can include a clip, a friction or pressure fit coupling, a threaded portion configured to receive a corresponding threaded portion of the flow cell 132, or a variety of other connectors known in the art or yet to be devised. The flow cell 132 can be a capillary flow cell, and at least part of the flow cell can comprise a transparent material (e.g., fused silica or glass) that allows the light beams 118, 119, 120 to enter the flow cell 132 and interact with a sample fluid contained within the flow cell 132. The flow cell 132 can be a thin hollow tube, forming a flow path that has a diameter of about 10 µm. Other flow cell types and/or sizes can be used, and the flow cell 132 can be oriented differently than as shown in FIG. 1. In some embodiments, the beams of light 118, 119, 120 strike the flow cell over areas centered about 110 µm to about 140 µm apart from each other, and in some embodiments, about 125 µm apart from each other. In some embodiments, the beams of light 118, 119, 120 strike the flow cell over areas centered about 100 µm to about 150 µm apart from each other. In some embodiments, the beams of light 118, 119, 120 strike the flow cell over areas centered about 100 µm to about 500 µm apart from each other. In some embodiments, the beams of light 118, 119, 120 strike the flow cell over areas centered up to about 500 µm apart from each other. In some embodiments, the thermal expansion coefficient of the thermally stable enclosure 150 matches the thermal expansion coefficient of the flow cell 132. Matching of thermal expansion coefficients may help reduce overall stress on the flow cell. For some forms of optical measurements, it may be desirable for the different laser beams to be focused to different locations in the flow cell 132 at specific locations (e.g., areas spaced about 125 µm apart).

Figure 2A:
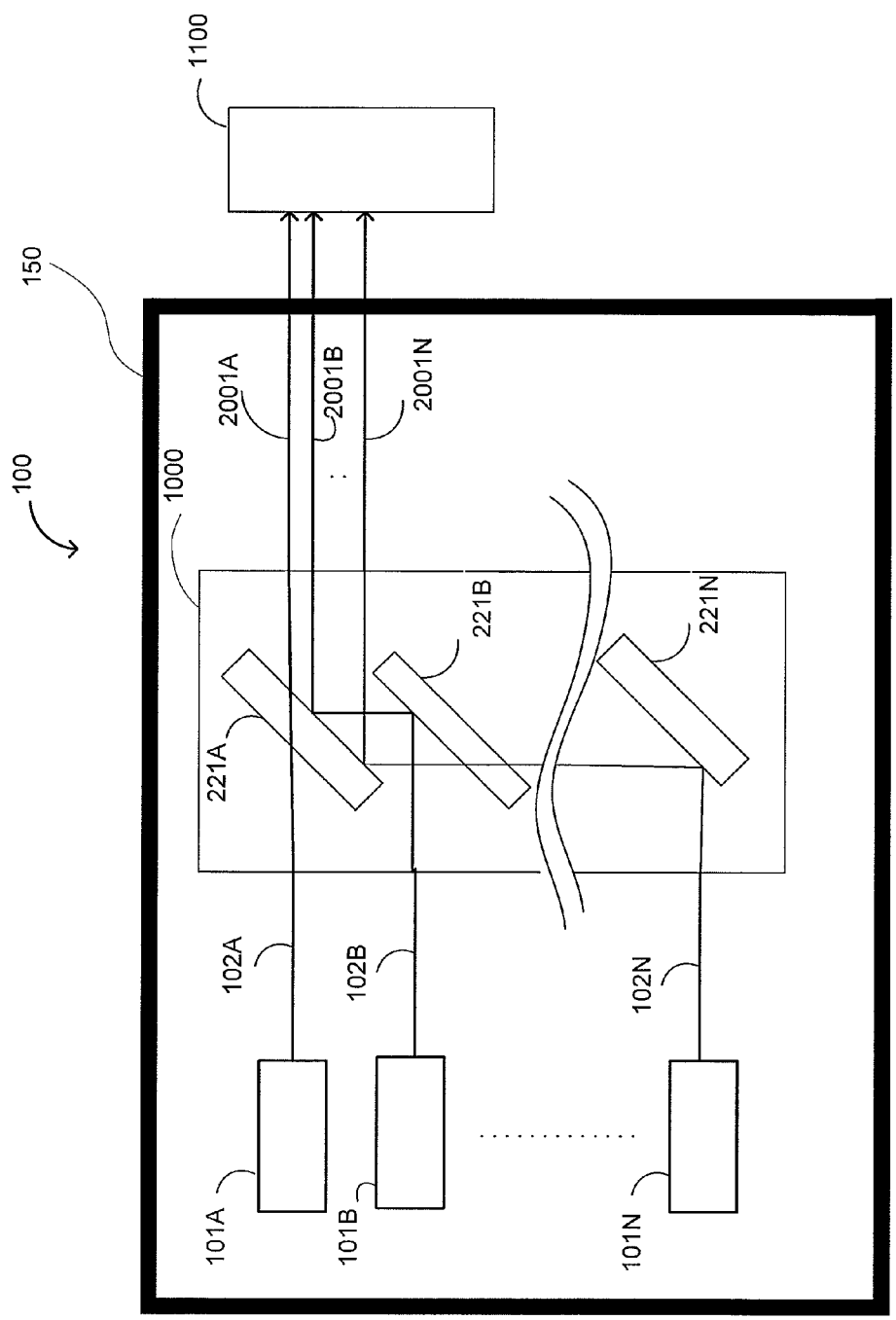
FIG. 2A depicts another example embodiment of a multi-laser system in which the beam positioning/combining system comprises mirrors.

FIG. 2A depicts another example embodiment of a multi-laser system in which the beam positioning/combining system comprises mirrors. As shown in FIG. 2A, a beam positioning combiner system that employs mirrors mounted onto a frame may be used. In various embodiments, the frames on which the mirrors are mountable may be adjustable, e.g., translatable, tiltable, etc. In various embodiments, the wavelength selective mirrors have significantly different reflection or transmission properties at different wavelengths. Accordingly, the wavelength selective mirrors can separate or combine laser beams with different wavelengths.

Through the use of suitable optical coatings, wavelength selective minors will selectively reflect (or transmit) light of at least one wavelength and not light of at least one other wavelength. In other embodiments, the wavelength selective minors may comprise mirrors with selectivity for a different number of wavelengths. The example embodiment of FIG. 2A depicts a plurality of wavelength-selective mirrors. The mirrors can be used to separate or combine lasers with different wavelengths. Alternatively, substantially non-wavelength selective mirrors that do not selectively reflect (or transmit) light of one laser and not light of another laser may be inserted in the path of the beam to redirect and/or alter the beam path or the beam. Other optical elements can also be inserted into the optical path.

The wavelength-selective mirrors 221A, 221B . . . 221N are configured with highly reflective and anti-reflective coatings in accordance with the wavelengths of the plurality of laser beams 102A, 102B . . . 102N. As shown in FIG. 2A, wavelength selective mirror 221A is configured to be highly reflective of the wavelength of the laser beams 102B through 102N and anti-reflective of the wavelength of laser beam 102A; wavelength-selective mirror 221B is configured to be highly reflective of the wavelength of the laser beam 102B and anti-reflective of the wavelength of the laser beam 102N;

and wavelength selective mirror 221N is configured to be highly reflective of the wavelength of the laser beam 102N. Other configurations are possible.

In the multi-laser system 100 shown in FIG. 2A, a plurality of optical paths are depicted. A first optical path originates at laser 101A and is transmitted through wavelength selective mirror 221A and transmitted toward the target object 1100. A second optical path originates at laser 101B, is then reflected at wavelength selective mirrors 221B and 221A, and transmitted toward the target object 1100. An n-th optical path originates at laser 101N, is then reflected at wavelength selective mirror 221N, transmitted at wavelength selective mirror 221B, reflected at wavelength selective mirror 221A, and transmitted toward the target object 1100. Propagating along these paths, laser beams 102A-102N, which may have originally been far from one another, are repositioned to be closer together as beams 2001A-2001N.

The mirrors may be configured to adjust the position of the plurality of laser beams to be at a certain distance of one another, for example in addition to the spacing adjustment that may be provided by placing the lasers at different heights within the enclosure. In some embodiments, the laser beams can be positioned to be coaxial, slightly offset but parallel to each other, or slightly offset but not parallel to each other.

Figure 2B:
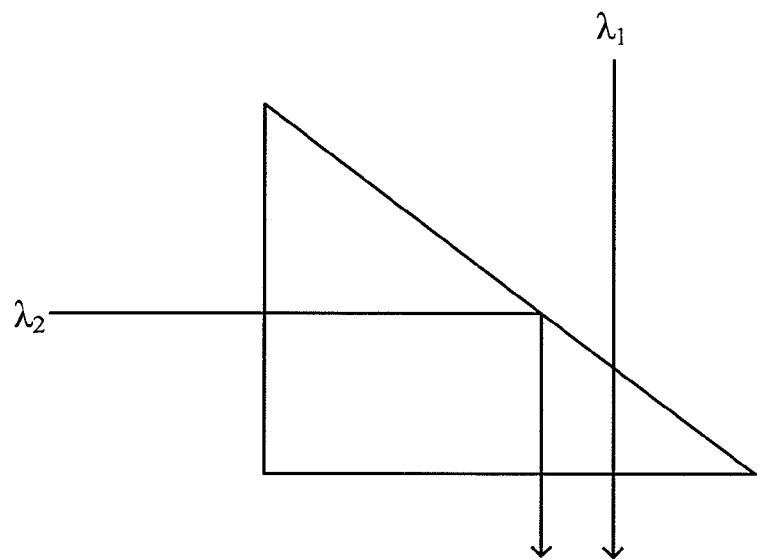
FIG. 2B depicts an example embodiment of a triangular prism.

FIG. 2B depicts an embodiment of a triangular prism. The prism is a transparent optical element comprising a substantially transparent optical material. The prism has flat, polished surfaces that reflect and/or refract light. One or more of these surfaces may be coated with an optical coating such as an interference coating that is reflective and/or anti-reflective. In some embodiments the coating is wavelength selective. For example, the prism may be configured to be highly reflective for certain wavelengths (e.g., of a first laser), and highly anti-reflective for other wavelengths (e.g., of a second laser). The exact angles between the surfaces depend on the application. As shown, the triangular prism generally has a triangular base and rectangular sides. Prisms may be made out of glass, or any material that is transparent to the wavelengths for which they are designed. In some embodiments, the material may include one of polymer, polycarbonate, polyethylene terephthalate, glycol-modified polyethylene terephthalate, amorphous thermoplastic, and/or other substrates. Prisms can be used to reflect light, and to split light into components with different, e.g., wavelength, polarizations. As illustrated in FIG. 2B, a triangular prism includes a glass surface configured to allow transmission of a laser beam of a given wavelength. The surface may be coated with a reflective coating to allow for the reflection of the laser beam of a different wavelength. In some embodiments, each of the wavelength selective mirrors illustrated in FIGS. 2 and 2A may be replaced with a triangular prism as the one illustrated in FIG. 2B. Triangular prisms may also be used that reflect a plurality of wavelength, for example, using total internal reflection. Accordingly, the prisms may be used to redirect laser beams and not for wavelength selection in various cases.

Figure 2C:
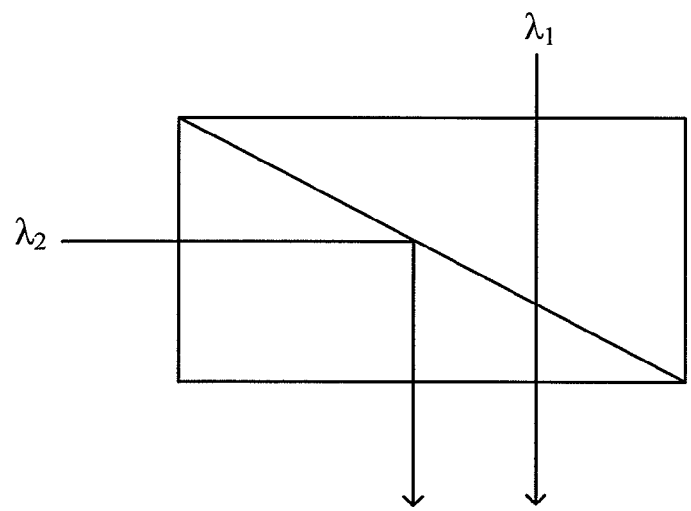
FIG. 2C depicts an example embodiment of a rectangular prism.

FIG. 2C depicts an embodiment of a rectangular prism. This rectangular prism comprises two triangular prisms contacted together. As illustrated in FIG. 2C, a rectangular prism may be used to deflect a beam of light, for example, by 90 degrees, although other angles are also possible. As described above, in some embodiments, prisms employ total internal reflection at the surfaces rather than for dispersion. If light inside the prism hits one of the surfaces at a sufficiently steep angle (greater than the critical angle), total internal reflection occurs and all of the light is reflected. This makes a prism a useful substitute for a mirror in some situations. As described above, triangular prisms or prisms having other shapes can also be used for this purpose. In some embodiments, rectangular prisms can be wavelength selective. For example, the interface between the two triangular prisms or prism portions that make up the rectangular prism shown in FIG. 2C can include an optical coating such as an interference coating that is wavelength selective. In some embodiments, for example, the rectangular prism selectively reflects one laser wavelength and selectively transmits another wavelength. Accordingly, the rectangular prism may include one or more coatings that are highly reflective for one or more laser wavelength. The rectangular prism may include one or more coatings that are anti-reflective for one or more laser wavelength. In some embodiments, each of the wavelength selective mirrors illustrated in FIGS. 2 and 2A may be replaced with a rectangular prism such as the one illustrated in FIG. 2C. Other arrangements and configurations are also possible. For example, a prism (e.g., a rectangular prism) may comprise two or more triangular or other shape prisms that are contacted together.

Figure 2D:
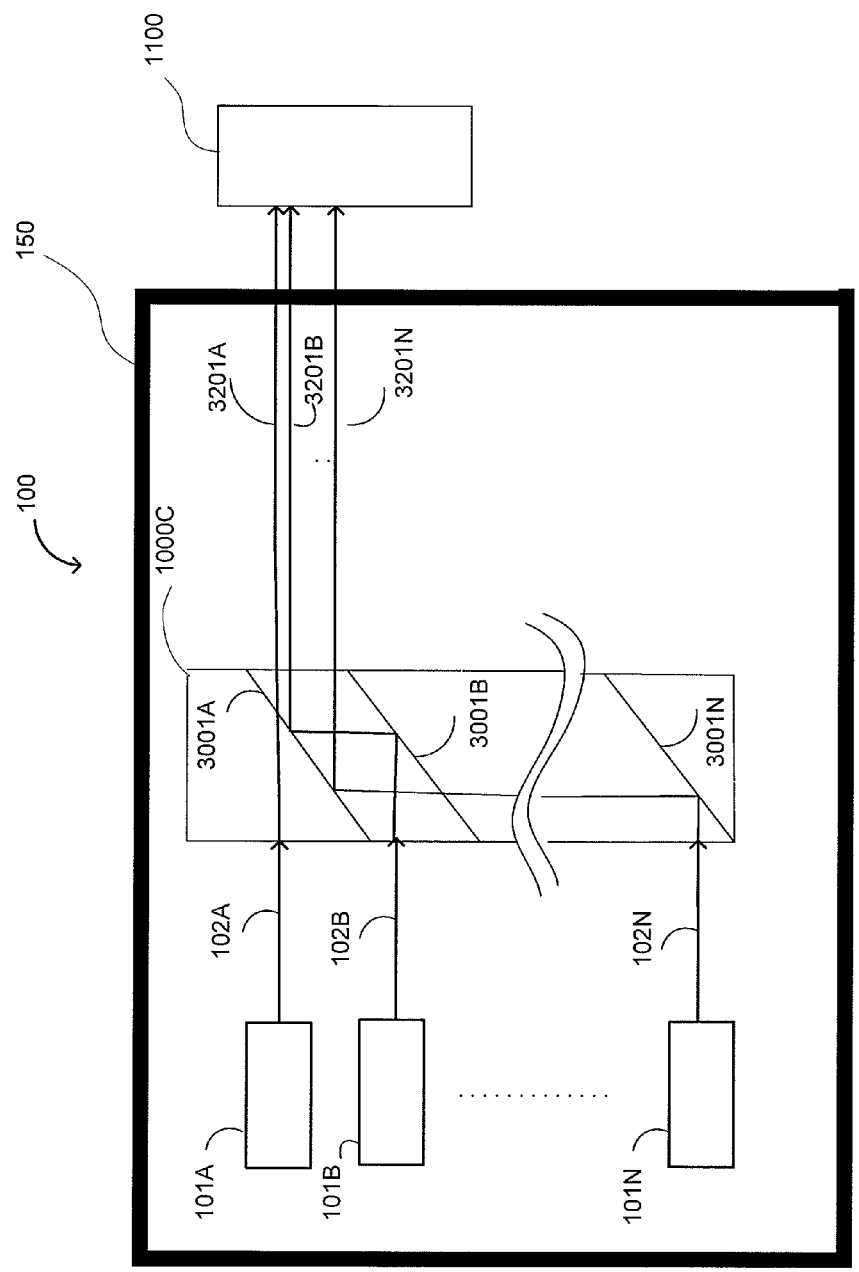
FIG. 2D depicts an example embodiment of a multi-laser system including a prism beam positioning/combining system.

FIG. 2D depicts an embodiment of the multi-laser system including a prism or prism bar beam positioning/combining system 1000C. As shown in FIG. 2D, a prism-based beam positioning combiner system is used to allow the lasers to be arranged in a row at one end of the temperature controlled enclosure. In some embodiments, the prism beam positioning/combining system may include optically contacted prisms having one or more surfaces coated to allow for the selective transmission or reflection of the laser beams. By proper selection of the surface coatings (such as for example wavelength selective reflective interference coatings), various lasers of different wavelength may be combined and output from the prism beam positioning/combining system. The prism beam positioning/combining system may also be configured and arranged with respect to the lasers and the respective laser beam paths such that the laser beams can be positioned such that they are, for example, closely spaced and/or parallel or co-linear on the output side of the prism-based beam positioning combiner system. In other embodiments, the prism beam positioning/combining system can be configured to position the beams in converging or diverging with respect to one another.

The prism illustrated in FIG. 2D may comprise a plurality of prisms or prism portions contacted or adhered together (e.g., using optical contact bonding, or optical adhesive at optical interfaces, and the like) to make a monolithic multi-prism beam combiner, or an aggregated prism. In some embodiments, a monolithic multi-prism may comprise 2, 3, 4, 5, or more prism portions. For example, a monolithic multi-prism may comprise N+1 or N+2 prism portions, where N is the number of lasers. In some embodiments, a monolithic multi-prism may comprise 1, 2, 3, 4, or more optical interfaces. For example, a monolithic prism may comprise N or N+1 optical interfaces, where N is the number of lasers. In various embodiments, one or more interface between the prism portions may be wavelength selective. For example, various of the prism portions may be configured to have one ore more wavelength selective surfaces with one or more highly reflective and/or an anti-reflective (e.g., interference) coatings in accordance with the wavelengths of the plurality of laser beams 102A-102N. As shown in FIG. 2D, the wavelength selective internal surface 3001A may be configured to be highly anti-reflective of the wavelength of the laser beam 102A and highly reflective of the wavelengths of laser beams 102B-102N. The wavelength selective internal surface 3001B may be configured to be highly reflective of the wavelength of the laser beam 102B. The wavelength selective surface internal surface 3001N may be configured to be highly reflective of the wavelength of the laser beam 102N.

In the embodiment shown in FIG. 2D, various prisms are contacted together (e.g., using cement, adhesive (e.g., optical adhesive), optical contact bonding) to form a monolithic multi-prism beam combiner or an integrated or aggregated prism in the shape of a rectangular structure or bar having a rectangular base and rectangular sides. The different prisms that are contacted together may have different shapes. Some of the prisms, for example, may have a base in the shape of a parallelogram and rectangular sides. Some of the other prisms may have different shaped bases and rectangular sides. For example, at least one triangular prism is shown. Other shapes and configurations are also possible.

In the multi-laser system 100 shown in FIG. 2D, a plurality of optical paths are depicted. A first optical path originates at laser 101A, is transmitted through a prism portion to the internal surface 3001A, and then is transmitted toward the target object 1100. A second optical path originates at laser 101B, then is reflected at internal surfaces 3001A and 3001B, and then is transmitted toward the target object 1100. An n-th optical path originates at laser 101N, is transmitted through internal surfaces 101B through 101N−1, then is reflected at internal surface 3001A, and then is transmitted toward the target object 1100. Propagating along these paths, laser beams 102A-102N, which may have originally been far from one another, are repositioned to be closer together as beams 3201A-3201N.

The prisms and interfaces therebetween within the prism-based beam positioning/combining system are configured to adjust the position of the plurality of laser beams to be at a certain distance from one another, in addition to the spacing adjustment that may be provided by placing the lasers at different heights within the enclosure. In some embodiments, the laser beams can be positioned to be coaxial, slightly offset but parallel to each other, or slightly offset but not parallel to each other.

Figure 2E:
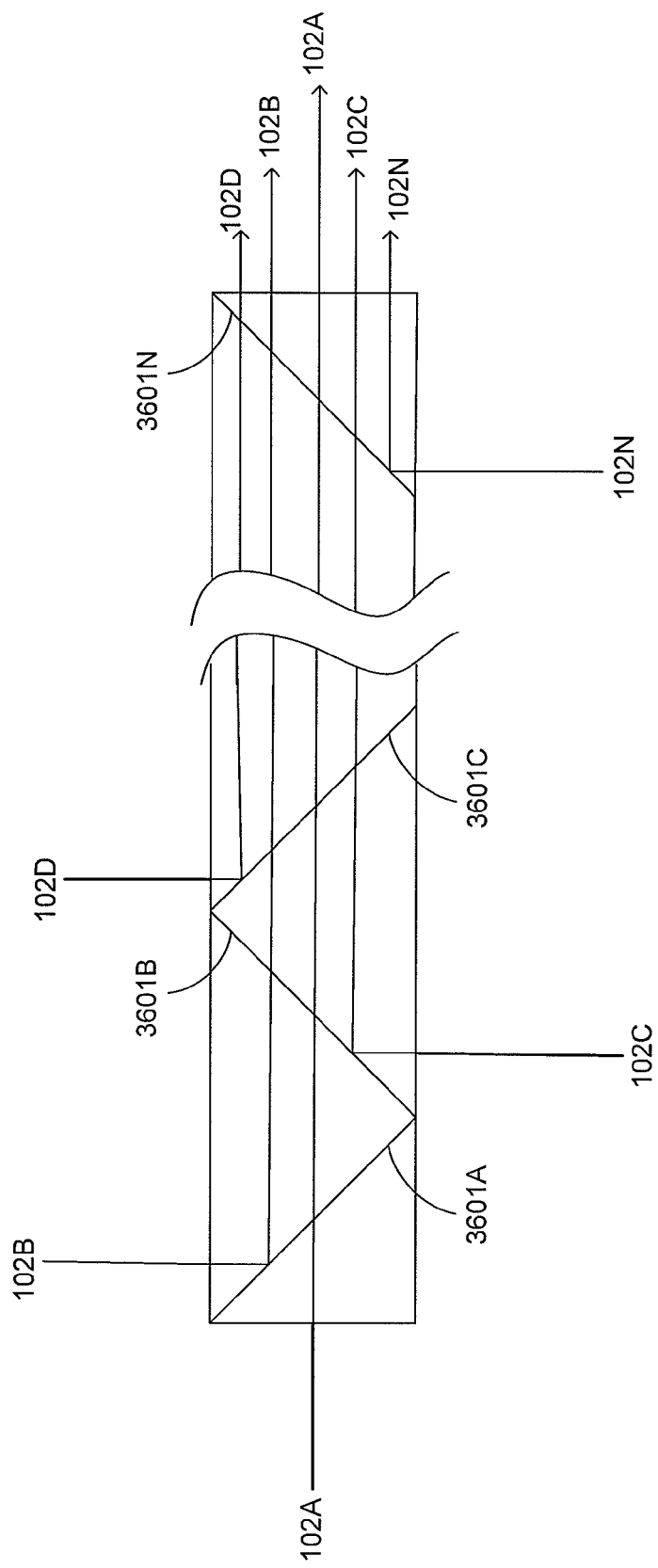
FIG. 2E depicts an example embodiment of a prism beam positioning/combining system.

FIG. 2E depicts another embodiment of a prism beam positioning/combining system. As shown in FIG. 2E, a prism-based beam positioning combiner system is used to allow the lasers to be spread out over the surface of the temperature controlled enclosure's base plate. The surfaces of the prisms may be coated to allow for the transmission or reflection of the laser beams. The prism illustrated in FIG. 2E may comprise a plurality of prisms or prism portions contacted or adhered together to make an aggregated prism or a monolithic multi-prism beam combiner. In various embodiments, one or more interface between the prism portions may be wavelength selective. For example, various of the prism portions may be configured to have one ore more wavelength selective surfaces with one or more highly reflective and/or an anti-reflective (e.g., interference) coatings in accordance with the wavelengths of the plurality of laser beams 102A-102N. As shown in FIG. 2E, the wavelength selective internal surface 3601A may be configured to be highly anti-reflective of the wavelength of the laser beam 102A and highly reflective of the wavelength of laser beam 102B. The wavelength selective internal surface 3601B may be configured to be highly anti-reflective of the wavelength of the laser beams 102A and 102B and highly reflective of the wavelength of laser beam 102C. The wavelength selective surface internal surface 3601C may be configured to be highly anti-reflective of the wavelength of the laser beams 102A, 102B, and 102C, and highly reflective of the wavelength of the laser beam 102D. The wavelength selective surface internal surface 3601N may be configured to be highly anti-reflective of the wavelength of the laser beams 102A, 102B, 102C, through 102N−1, and highly reflective of the wavelength of the laser beam 102N.

In the embodiment shown in FIG. 2E, various prisms are contacted together (e.g., using cement, adhesive (e.g., optical adhesive), optical contact bonding) to form an integrated or aggregated prism in the shape of a rectangular structure or bar having a rectangular base and rectangular sides, or a monolithic multi-prism beam combiner. The different prisms that are contacted together have different shapes. For example, different triangular prisms are shown. Some of the prisms, for example, may have a base in the shape of a right angle triangle and rectangular sides while other prisms may have a base in the shape of an equilateral triangle and have rectangular sides. Other shapes and configurations are also possible.

In the multi-laser system 100 shown in FIG. 2E, a plurality of optical paths are depicted. A first optical path originates at laser 101A, is transmitted through prism portions and internal surfaces 3601A, 3601B, 3601C through 3601N, and is transmitted toward the target object 1100. A second optical path originates at laser 101B, is then reflected at internal surface 3601A, transmitted through prism portions and internal surfaces 3601B, 3601C through 3601N, and toward the target object 1100. A third optical path originates at laser 101C, is then reflected at internal surface 3601B, transmitted through prism portions and internal surfaces 3601C through 3601N, and toward the target object 1100. A fourth optical path originates at laser 101D, is reflected at internal surface 3601C, transmitted through prism portions and internal surfaces 3601D through 3601N, and toward the target object 1100. An n-th optical path originates at laser 101N, is reflected at internal surface 3601N, and transmitted toward the target object 1100. Propagating along these paths, laser beams 102A-102N, which may have originally been coming from different directions and far from one another, are repositioned to be closer together as beams 3701A-3701N. As described herein, the laser beams 102A-102N may also be repositioned to be parallel to each other as beams 3701A-3701N.

A wide range of other aggregated prisms (or monolithic multi-prism beam combiners) comprising a plurality of prism portions contacted together are also possible. Aggregated prisms (or monolithic multi-prism beam combiners) may include optical coating for example at interfaces between prism portions or prisms that make up the aggregated prism. These optical coatings may be wavelength selective reflective coating or may be anti-reflective (AR) coatings. One example of such an aggregated prism comprising a plurality or prisms or prism portions contacted together is the X-prism. Other aggregated prisms, however, may also be used.

A multi-prism beam combiner may be more advantageous than beam combiners using separate dichroic mirrors mounted in individual flexure mounts, mounted using a glue-block approach, or all mounted in a common mount. In a multi-prism beam combiner, all of the reflective surfaces are tied together so that the number of opto-mechanical components that can contribute to the relative movement of the laser beams with respect to each other is greatly reduced thereby improving the system performance. Additionally, the reduced parts count and reduced complexity make for increased ease of manufacturing and should allow for a decrease in system size. Furthermore, the number of surfaces exposed to possible contamination is reduced. Also, the relatively large size of the prism combiner compared to an individual dichroic mirror reduces the impact that the coefficient of thermal expansion (CTE) mismatch between most adhesives, the optics and the metal used in the optical mounts has on beam position.

Figure 3:
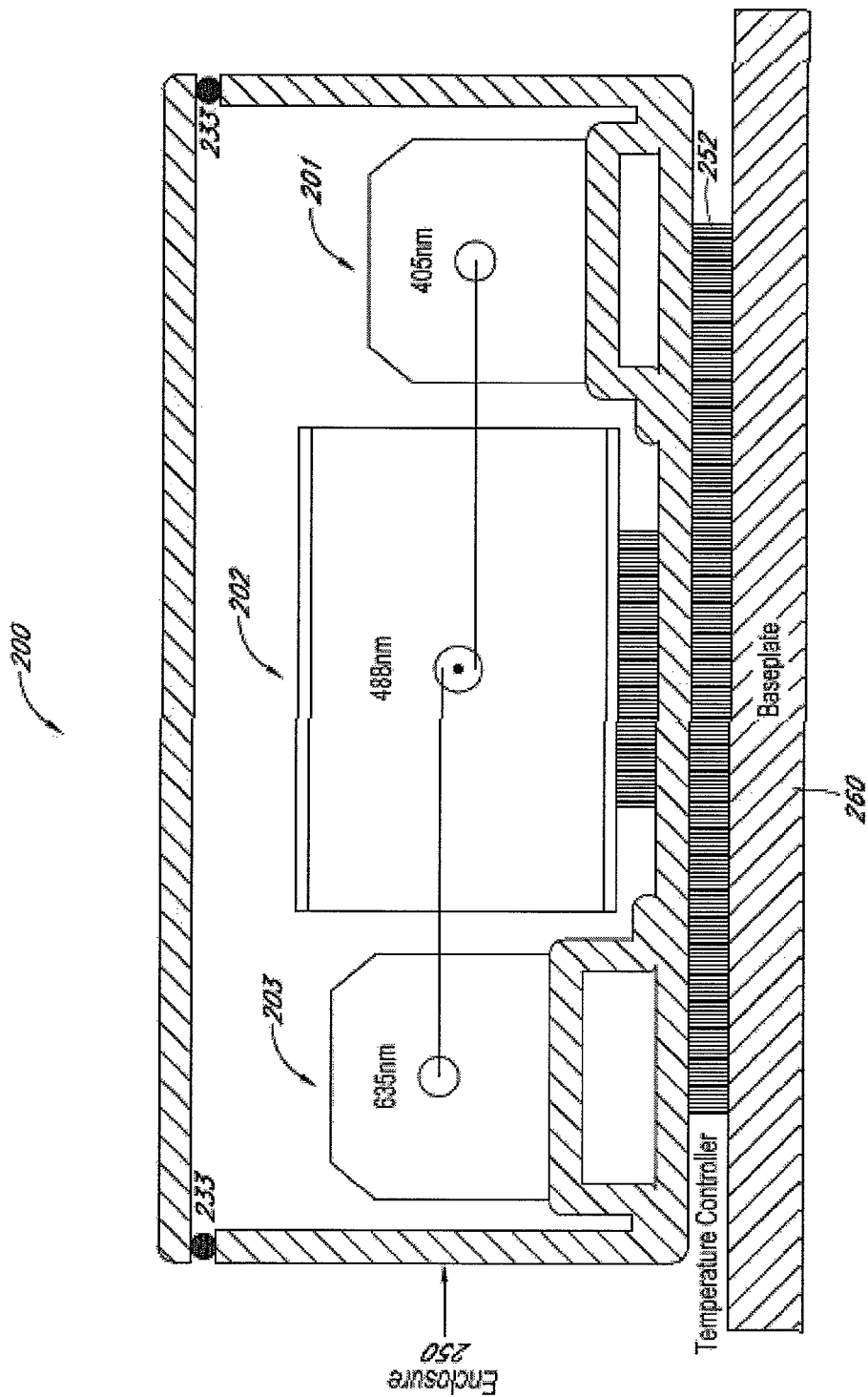
FIG. 3 depicts the front view of the system of FIG. 2.

FIG. 3 depicts the front view of the multi-laser system 100 depicted in FIG. 2. As described above, in some embodiments, the thermally stable enclosure 250 is hermetically sealed. The hermetic sealing may be provided by o-rings 233.

Again, hermetically sealing can reduce particles and contamination from outside the enclosure. Moreover, as described above, a hermetic seal may also reduce or prevent the flow of air currents and thus prevent or reduce the flow of ambient temperature changes into the enclosure. This in turn may reduce temperature instability within the enclosure. In some embodiments, the top of enclosure 250 may be thermally coupled, possibly with a copper braid, to the main body of the enclosure 250 to reduce thermal effects.

As shown in FIG. 3, the multi-laser system may further comprise a temperature controller 252. In some embodiments, the temperature controller 252 may comprise a thermo electric cooler (TEC), a temperature sensor and control electronics. The TEC may pump heat from one side to the other depending on the direction of current flow through the TEC. The direction of current flow may be determined by the control electronics. In some embodiments, for example, if the ambient temperature were higher than the enclosure 250's set point temperature then the control electronics may direct current flow through the TEC so that heat was pumped out of the enclosure 250 thereby helping maintain the enclosure's set point temperature. In other embodiments, if the ambient temperature were lower than the enclosure 250's set point temperature, then the control electronics may reverse the current flow through the TEC so that heat was pumped into the enclosure 250 again helping maintain the enclosure's set point temperature. A temperature controller 252 can be thermally coupled to the thermally stable enclosure 250. The temperature controller 252 can include a temperature sensor (not shown) to measure the temperature of the thermally stable enclosure 250, and to provide feedback to the control electronics. In some embodiments, the temperature sensor may comprise a thermistor. The temperature controller 252 may remove heat from or add heat to the thermally stable enclosure 250 in order to maintain a substantially constant temperature in the thermally stable enclosure 250. The high thermal conductivity of the material of the enclosure 250 helps the temperature controller to relatively quickly adjust the temperature within the enclosure 250 in response to temperature variations outside of the enclosure 250 and also reduce the presence of temperature variations across the enclosure 250.

As shown in FIG. 3, the multi-laser system may also comprise a baseplate 260. The baseplate 260 may act as a thermal heat sink for the temperature controller 252.

In some embodiments, the temperature within the thermally stable enclosure 250 can be held stable to within ±1° C., ±2° C., ±3° C., ±5° C., etc., for example, of a target temperature. In some embodiments, the temperatures of the wavelength selective mirrors and the focusing optics can be held to be within ±1° C., ±2° C., ±3° C., ±5° C., etc. of one another. In some embodiments, the temperature over a substantial portion of the enclosure can be held to be within ±1° C., ±2° C., ±3° C., ±5° C., etc. In some embodiments, the temperature over the entire enclosure can be held to be within ±1° C., ±2° C., ±3° C., ±5° C., etc., for example, of a target temperature. In some embodiments, the temperature within the enclosure can be held to be within ±1° C., ±2° C., ±3° C., ±5° C., etc., for example, of a target temperature. In some embodiments, the temperature within the thermally stable enclosure 250 can be held within ±1° C. of the target temperature. In some embodiments, the target temperature can be between 10° C. and 50° C. In some embodiments, the target temperature can be between about 15° C. and about 45° C. In other embodiments, the target temperature can be between about 15° C. and about 35° C. In other embodiments, the target temperature can be between about 10° C. and about 40° C. The temperature controller 252 also maintains the focused laser beams aligned with respect to the flow cell over a wide range of ambient temperatures. In some embodiments, the range of ambient temperatures can be between about 10° C. and about 55° C. In some embodiments, the range of ambient temperatures can be between about 10° C. and about 50° C. In some embodiments, the range of ambient temperatures can be between about 15° C. and about 45° C. In other embodiments, the range of ambient temperatures can be between about 15° C. and about 35° C. In other embodiments, the range of ambient temperatures can be between about 10° C. and about 40° C.

FIG. 3 also depicts that the three lasers 201, 202, and 203 may be placed at different heights within the enclosure 250. The placement at different heights may assist in positioning the focused laser beams at a desired spacing from one another at the flow cell. By disposing the lasers at different heights, the focused beams at the flow cell may be separated by between about 110 µm and about 140 µm of one another. In some embodiments, the focused beams may be separated by between about 100 µm to about 150 µm of one another. In some embodiments, the focused beams may be separated by between about 100 µm to about 500 µm of one another. In some embodiments, the focused beams may be separated by up to about 500 µm of one another. The wavelength selective mirrors, however, can additionally be adjusted to account for the imperfection in laser positions that may result, for example, from manufacturing tolerances. Accordingly, the wavelength selective mirrors may establish better positioning of the beams directed onto the flow cell.

Figure 4:
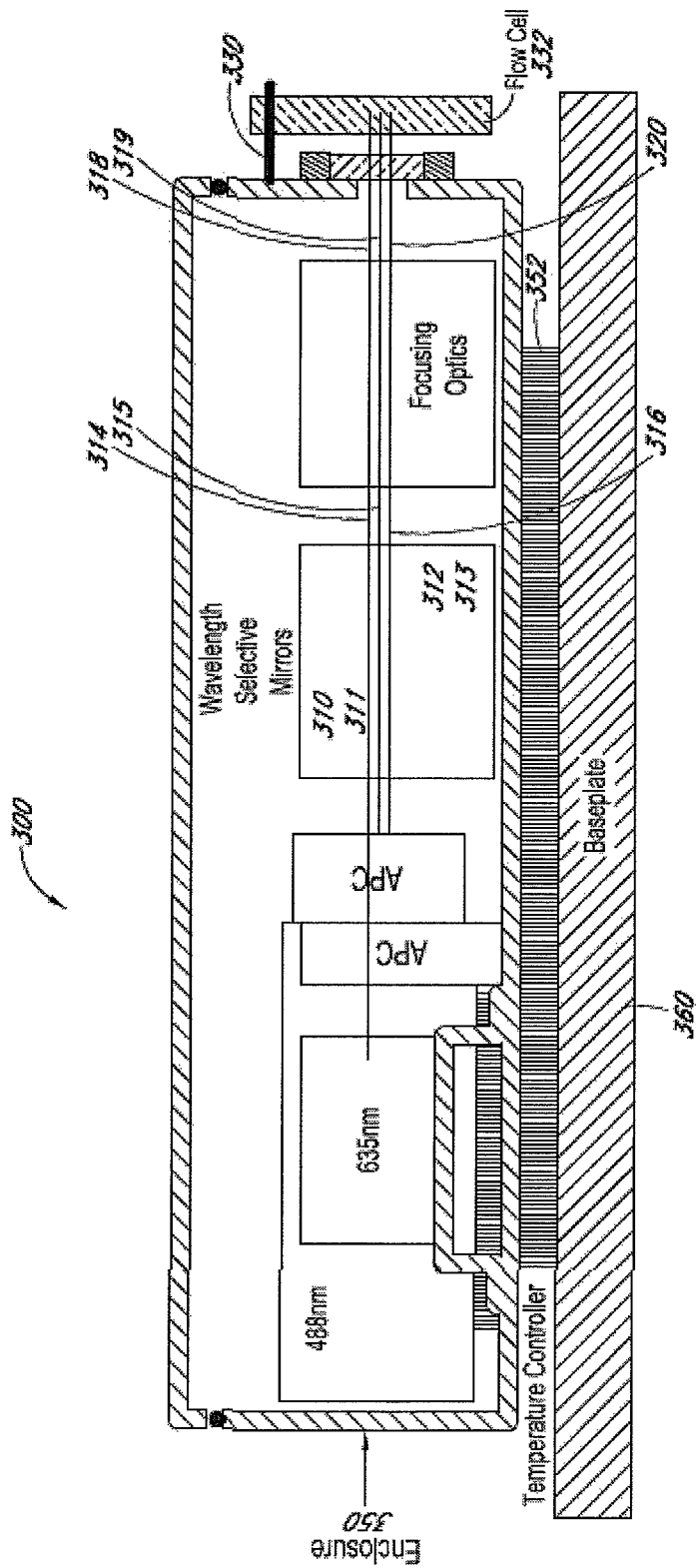
FIG. 4 depicts the side view of the system of FIG. 2.

FIG. 4 depicts the side view of the multi-laser system 100 depicted in FIG. 2. FIG. 4 also shows the placement of the lasers at different heights. The thermally stable enclosure 350 comprises wavelength selective mirrors 310, 311, 312, 313 that are configured to adjust the position of the plurality of laser beams 314, 315, 316 to be at a certain distance of one another, in addition to the spacing adjustment that may be provided by placing the lasers at different heights within the enclosure 350. In some embodiments, the laser beams can be positioned to be coaxial, slightly offset but parallel to each other, or slightly offset but not parallel to each other. In some embodiments, the plurality of focused laser beams 318, 319, 320 may be separated by about 110 µm and about 140 µm of one another. In some embodiments, the plurality of focused laser beams 318, 319, 320 may be separated by about 100 µm and about 150 µm of one another. In some embodiments, the plurality of focused laser beams 318, 319, 320 may be separated by about 100 µm and about 500 µm of one another. In some embodiments, the plurality of focused laser beams 318, 319, 320 may be separated by up to about 500 µm of one another. In some embodiments, the plurality of focused laser beams 318, 319, 320 may be positioned to be at a distance of about 125 µm of one another.

As can be seen in FIG. 4, the thermally stable enclosure 350 comprises a top, a bottom, and four sides. In some embodiments, the thermally stable enclosure 350 has a width of about 3 inches or less, a length of about 6 inches or less, and/or a height of about 2 inches or less. In other embodiments, the length, the width, and the height of the thermally stable enclosure 350 may be relatively larger or smaller. In some embodiments, the thermally stable enclosure 350 has a width of about 6 inches or less, a length of about 12 inches or less, and/or a height of about 3 inches or less. In some embodiments, the thermally stable enclosure 350 has a volume of 36 cubic inches ($in^3$) or less. With a relatively small volume, the temperature controller is better able to adjust the temperature of the enclosure and system in response to variations in ambient temperature. The temperature controller is thus able to avoid temporal variations in temperature induced by fluctuation in ambient conditions. The relatively small volume may reduce temperature instabilities within the enclosure 350 by reducing temperature gradients across the enclosure 350. In other embodiments, the volume of the thermally stable enclosure 350 may be relatively larger or smaller. Also shown in FIG. 4 is the flow cell connection 330, described above.

Figure 5:
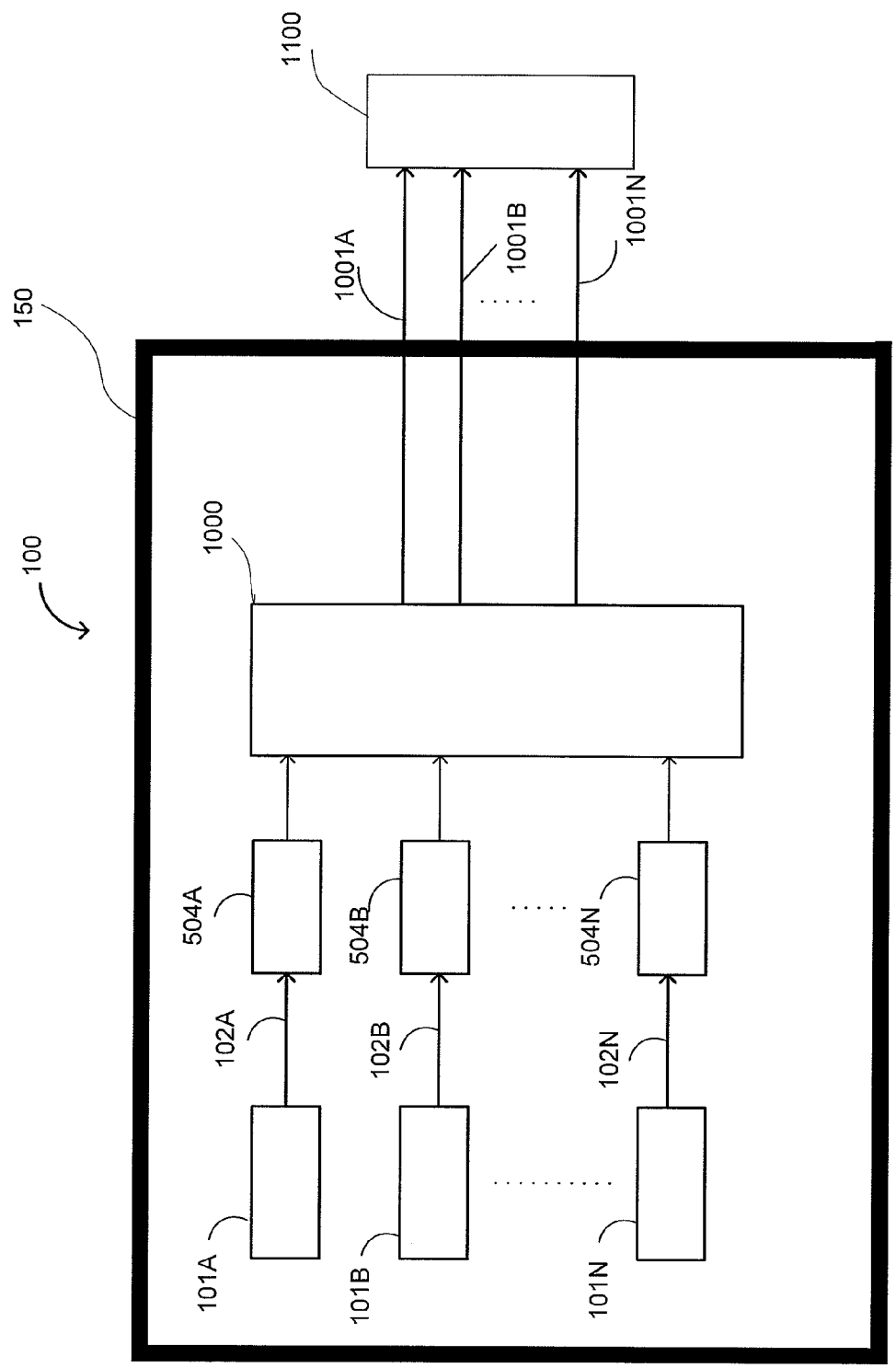
FIG. 5 depicts an example embodiment of a multi-laser system further including a plurality of beam adjusters.

FIG. 5 depicts an example embodiment of a multi-laser system further including an optional plurality of beam adjusters 504A-504N. In various embodiments, the boresight and centration errors of the n laser beams and/or the angular and lateral positioning errors of the opto-mechanical components may be compensated for by using the separate beam position adjusters 504A-504N. The adjusted laser beams may then be positioned and/or combined into a desired spatial arrangement by the beam positioning/combining system that a specific application requires.

Figure 6:
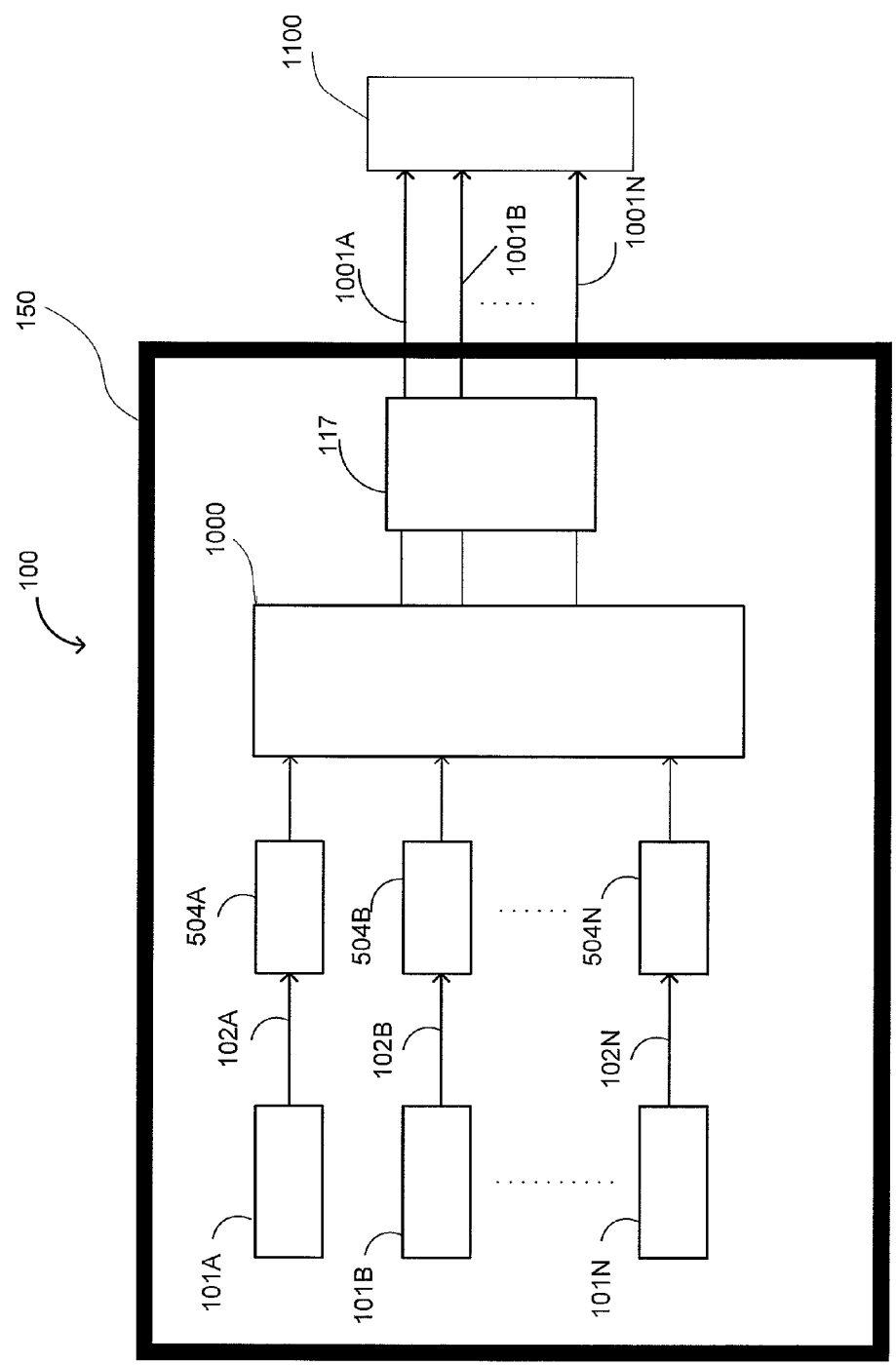
FIG. 6 depicts an example embodiment of a multi-laser system further including focusing optics.

FIG. 6 depicts the embodiment of the multi-laser system of FIG. 5 further including optional focusing or beam shaping optics 117. As described in relation to FIG. 2 above, beam focusing optics or beam shaping optics may be used to provide size reduction and/or shaping to the output laser beams. For example, the focusing/beam shaping optics may focus a laser beam down to a smaller spot. The focusing/beam shaping optics may also be used to change the shape of the laser beams.

The output laser beams depicted in FIG. 6 may have respective spot sizes of between about 55 μm and about 110 μm in one direction and between about 5 μm and about 15 μm in another direction (e.g., perpendicular to the one direction). In other embodiments, the laser beams may have respective spot sizes of between about 70 μm and about 110 μm in one direction and between about 5 μm and about 15 μm in another direction (e.g., perpendicular to the one direction). In other embodiments, the laser beams may have respective spot sizes of between about 50 μm and about 150 μm in one direction and between about 5 μm and about 20 μm in another direction (e.g., perpendicular to the one direction). In other embodiments, the laser beams may have spot sizes of between about 55 μm and about 100 μm in one direction and between about 5 μm and about 15 μm in another direction (e.g., perpendicular to the one direction). In other embodiments, the laser beams may have spot sizes of between about 70 μm and about 100 μm in one direction and between about 5 μm and about 15 μm in another direction (e.g., perpendicular to the one direction). In other embodiments, the laser beams may have respective spot sizes of between about 50 μm and about 150 μm in one direction and between about 5 μm and about 20 μm in another direction (e.g., perpendicular to the one direction). In some embodiments, the output laser beams 118, 119, 120 may have respective spot sizes of about 80 μm in one direction and about 10 μm in another direction (e.g., perpendicular to the one direction). In other embodiments, the output laser beams 118, 119, 120 may have respective spot sizes of about 100 μm in one direction and about 10 μm in another direction (e.g., perpendicular to the one direction). These may correspond to major and minor axes of an ellipse for a beam with an elliptical cross-section and spot shape. Other sizes and shapes are possible for the light beams.

Figure 7:
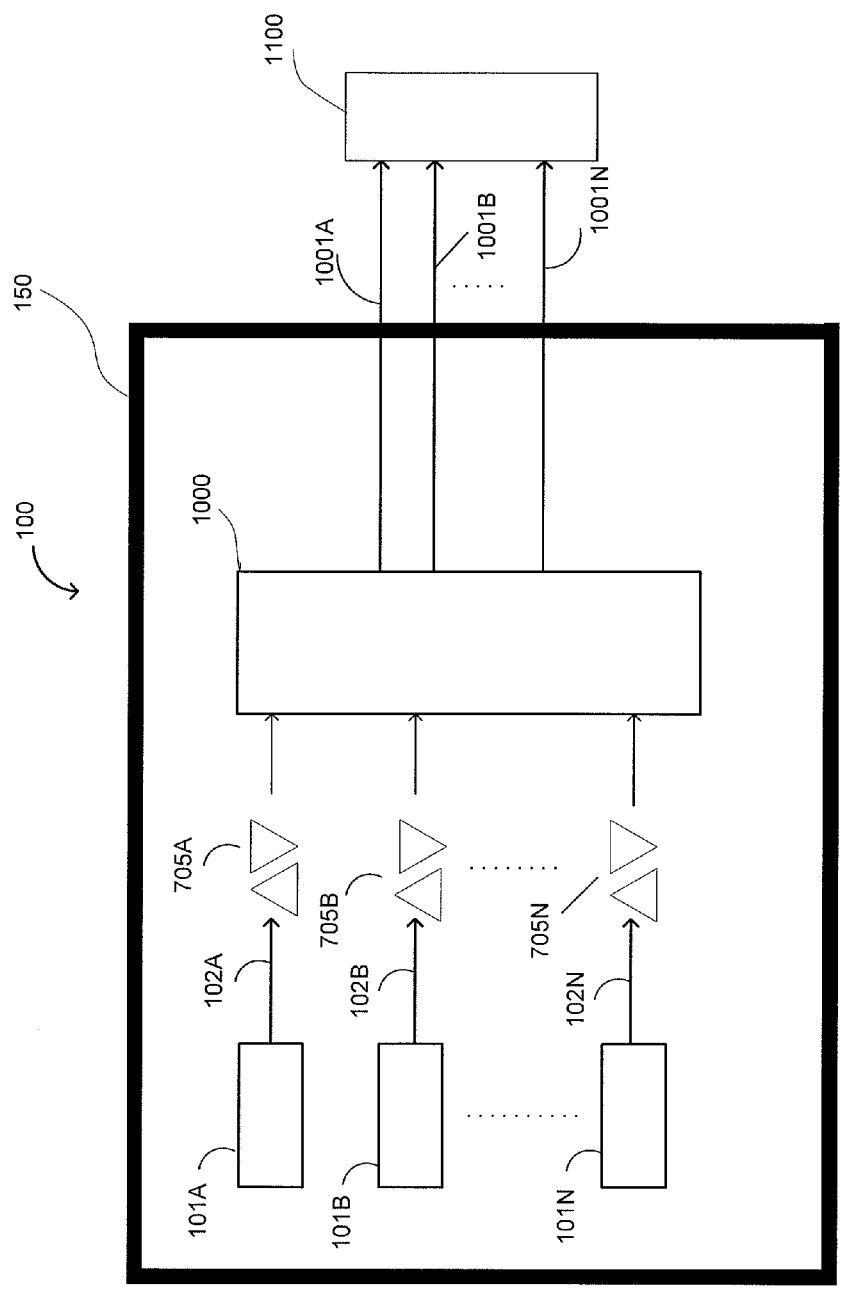
FIG. 7 depicts an example embodiment of a multi-laser system in which the beam adjusters comprise Risley prism pairs.

FIG. 7 depicts an example embodiment of a multi-laser system in which the beam adjusters 504A-504N comprise Risley prism pairs 705A-705N. In other embodiments, other systems may be used as the separate beam position adjusters 504A-504N. In various embodiments, the laser boresight and opto-mechanical angular errors may be compensated for by rotating the Risley prisms while the laser centration and opto-mechanical lateral positioning errors may be compensated for by adjusting the Risley prism assembly pitch, yaw, and/or separation between the individual prisms (e.g., by adjusting one or both of the individual prisms). The aligned laser beams may then be positioned or combined into a desired spatial arrangement that a specific application requires by the beam positioning/combining system.

FIG. 7 depicts a Risley prism pair used with each laser beam. In other embodiments, a different number of Risley prisms may be used. Other optical elements can also be inserted into the optical path.

In various embodiments, Risley prisms comprising wedged optics, usually used in pairs, to redirect optical beams are used. In various embodiments, an incoming light beam enters a Risley prism pair, experiences refraction and redirection under Snell's Law, and exits the Risley prism pair. In some configuration of the Risley prisms, there is just a translation of the output beam with respect to the input beam. If the arrangement of the Risley prisms with respect to each other is changes, the output beam may experience an elevation deviation. The ability to control azimuth may be provided by rotating the prism pair together. Therefore, the Risley prism pair can be used to direct a light beam at a variety of elevation angles and azimuthal angles.

The Risley prism pairs 705A-705N wedge angles and the azimuthal rotation between the prisms are determined in accordance with the respective laser beam 102A-102N. As shown in FIG. 6, Risley prism pair 705A is configured to adjust the laser beam 102A, Risley prism pair 705B is configured to adjust the laser beam 102B, and Risley prism pair 705N is configured to adjust the laser beam 102N.

In the multi-laser system 100 shown in FIG. 7, a plurality of optical paths are depicted. A first optical path originates at laser 101A, passes through the Risley prism pair 705A, where laser boresight, centration and opto-mechanical angular and lateral positioning errors may be compensated through adjustment of the wedge angles of and the azimuthal rotation between the prism pair 705A, and then arrives at the beam combining/positioning system 1000. A second optical path originates at laser 101B, passes through the Risley prism pair 705B, where laser boresight, centration and opto-mechanical angular and lateral positioning errors may be compensated through adjustment of the wedge angles of and the azmiuthal rotation between the prism pair 705B, and then arrives at the beam combining/positioning system 1000. An N-th optical path originates at laser 101N, passes through the Risley prism pair 705N, where laser boresight, centration and opto-mechanical angular and lateral positioning errors may be compensated through adjustment of the wedge angles of and the azimuthal rotation between the prism pair 705N, and then arrives at the beam combining/positioning system 1000.

Propagating along these paths, laser beams 102A-102N, which may have originally been far from one another, are repositioned to be closer together as beams 1001A-1001N. In some embodiments, the beams 1001A-1001N are parallel to one another. In other embodiments, the beams 1001A-1001N are not parallel to one another. Other optical components (e.g., lenses, prisms, polarization rotators, waveplates, etc.) can be included to alter the laser beams and/or optical paths.

Figure 8A:
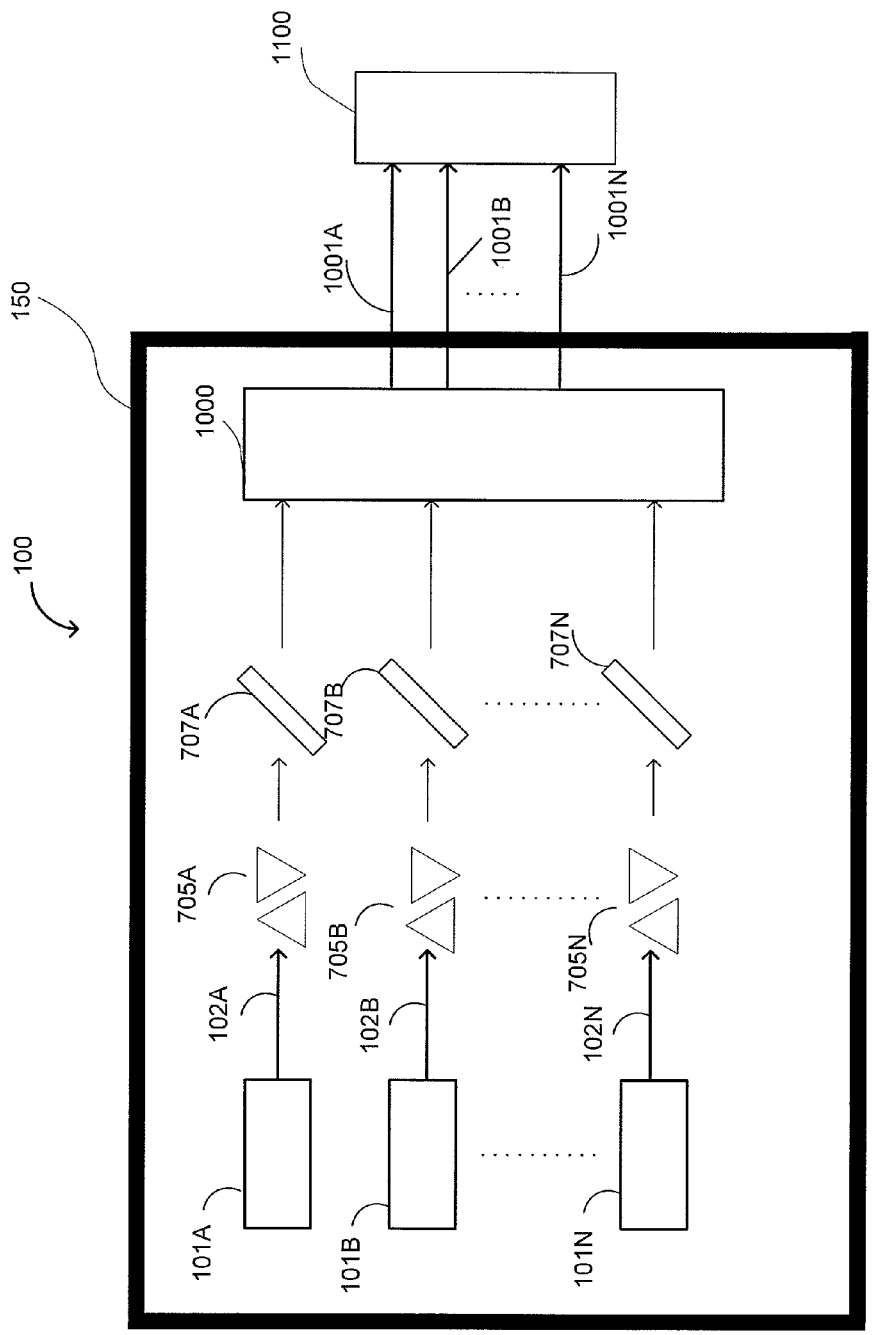
FIGS. 8A-8B depict example embodiments of a multi-laser system in which the beam adjusters comprise Risley prisms and plane parallel plates.
Figure 8B:
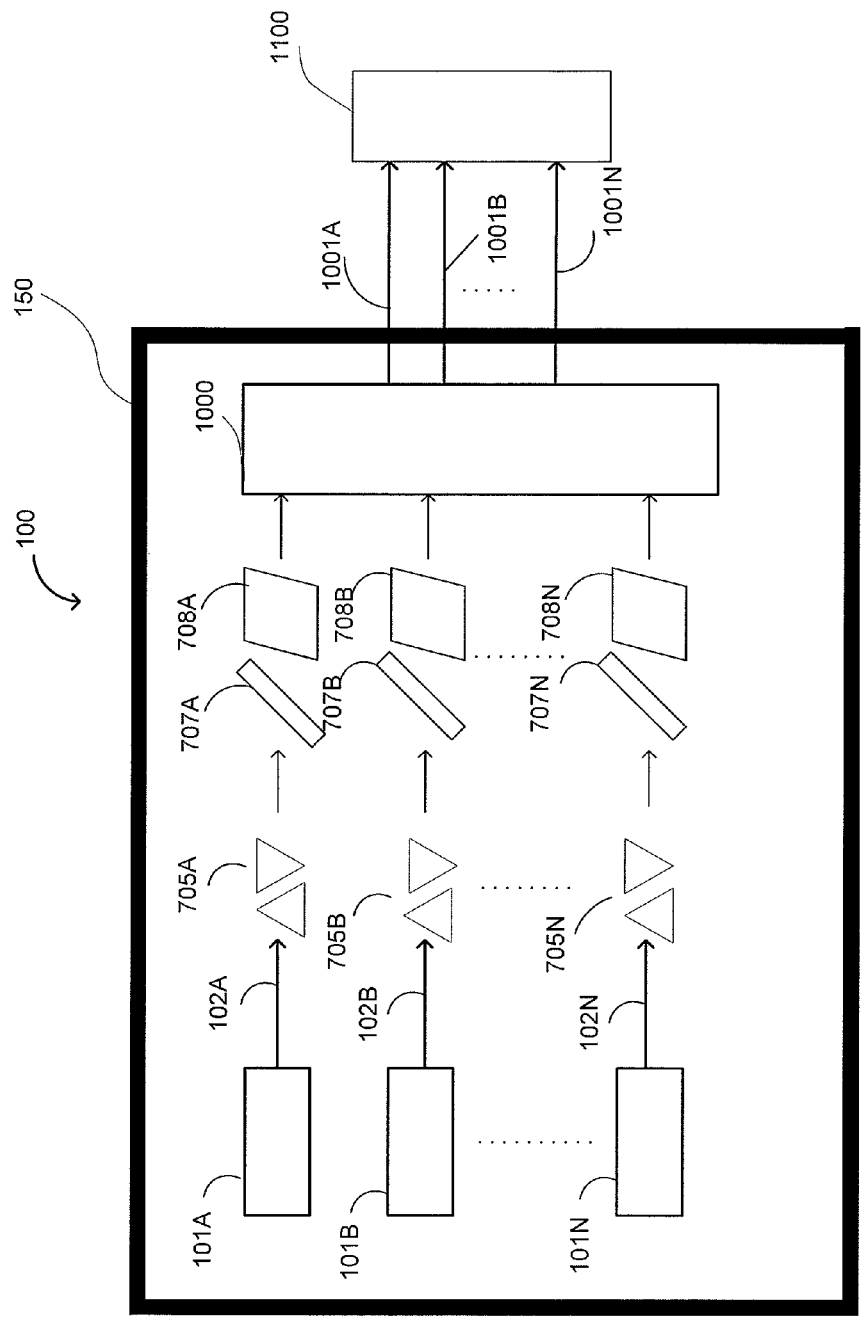

FIGS. 8A-8B depict example embodiments of a multi-laser system in which the beam adjusters comprise Risley prisms and plane parallel plates. In the embodiment of FIG. 8A, a combination of Risley prism pairs 705A-705N and glass etalon plates 707A-707N are used for the separate beam position adjusters 504A-504N illustrated in FIG. 5. In other embodiments, the etalon plates may be comprised of material other than glass. In some embodiments, the plane parallel plates may be made out of glass, or any material that is transparent to the wavelengths for which they are designed. In some embodiments, the material may include one of polymer, polycarbonate, polyethylene terephthalate, glycol-modified polyethylene terephthalate, amorphous thermoplastic, and/or other substrates. The etalon plates comprise plane parallel plates. Other optical elements may however be used in different embodiments. Adjustment of the beams may be provided, for by using the combination of Risley prism pairs as described in relation to FIG. 7 above, and glass etalon plates 707A-707N. In the embodiment of FIG. 8A, a single glass etalon plate may be used for providing correction to lateral positioning errors in both x and y planes. In the embodiment of FIG. 8B, a separate glass etalon plate is used for correcting later positioning errors in each (e.g., by being tiltable along one axis) of the x and y planes or in both (e.g., by being tiltable along multiple axes) of the x and y planes.

In various embodiments, the laser boresight and opto-mechanical angular errors may be compensated for by rotating the prisms while the laser centration and opto-mechanical lateral positioning errors may be compensated for by adjusting the pitch and/or yaw of the parallel optical plate. The aligned laser beams may then be positioned or combined into a desired spatial arrangement by the beam positioning/combining system that a specific application requires.

In the multi-laser system 100 shown in FIG. 8A, a plurality of optical paths are depicted. A first optical path originates at laser 101A, passes through the Risley prism pair 705A, where laser boresight and opto-mechanical angular errors may be compensated through adjustment of the wedge angles of the prism pair 705A, passes through the glass etalon plate 707A, where laser centration and opto-mechanical lateral positioning errors may be compensated for by adjusting the pitch and/or yaw of the glass etalon plate 707A, and then arrives at the beam combining/positioning system 1000. A second optical path originates at laser 101B, passes through the Risley prism pair 705B, where laser boresight and opto-mechanical angular errors may be compensated through adjustment of the wedge angles of the prism pair 705B, passes through the glass etalon plate 707B, where laser centration and opto-mechanical lateral positioning errors may be compensated for by adjusting the pitch and/or yaw of the glass etalon plate 707B, and then arrives at the beam combining/positioning system 1000. An N-th optical path originates at laser 101N, passes through the Risley prism pair 705N, where laser boresight, and opto-mechanical angular errors may be compensated through adjustment of the wedge angles of the prism pair 705N, passes through the glass etalon plate 707N, where laser centration and opto-mechanical lateral positioning errors may be compensated for by adjusting the pitch and/or yaw of the glass etalon plate 707N, and then arrives at the beam combining/positioning system 1000.

In the multi-laser system 100 shown in FIG. 8B, a plurality of optical paths are depicted. A first optical path originates at laser 101A, passes through the Risley prism pair 705A, where laser boresight and opto-mechanical angular errors may be compensated through adjustment of the wedge angles of the prism pair 705A, passes through glass etalon plates 707A, 708A, where laser centration and opto-mechanical lateral positioning errors may be compensated for by adjusting the pitch and/or yaw of the glass etalon plates 707A and/or 708A, and then arrives at the beam combining/positioning system 1000. A second optical path originates at laser 101B, passes through the Risley prism pair 705B, where laser boresight and opto-mechanical angular errors may be compensated through adjustment of the wedge angles of the prism pair 705B, passes through glass etalon plates 707B, 708B, where laser centration and opto-mechanical lateral positioning errors may be compensated for by adjusting the pitch and/or yaw of the glass etalon plates 707B and/or 708B, and then arrives at the beam combining/positioning system 1000. An N-th optical path originates at laser 101N, passes through the Risley prism pair 705N, where laser boresight, and opto-mechanical angular errors may be compensated through adjustment of the wedge angles of the prism pair 705N, passes through glass etalon plates 707N, 708N, where laser centration and opto-mechanical lateral positioning errors may be compensated for by adjusting the pitch and/or yaw of the glass etalon plates 707N and/or 708N, and then arrives at the beam combining/positioning system 1000.

Propagating along these paths, laser beams 102A-102N, which may have originally been far from one another, are repositioned to be closer together as beams 1001A-1001N. In some embodiments, the beams 1001A-1001N are parallel to one another. In other embodiments, the beams 1001A-1001N are not parallel to one another. Other optical components (e.g., lenses, prisms, polarization rotators, waveplates, etc.) can be included to alter the laser beams and/or optical paths.

Figure 9:
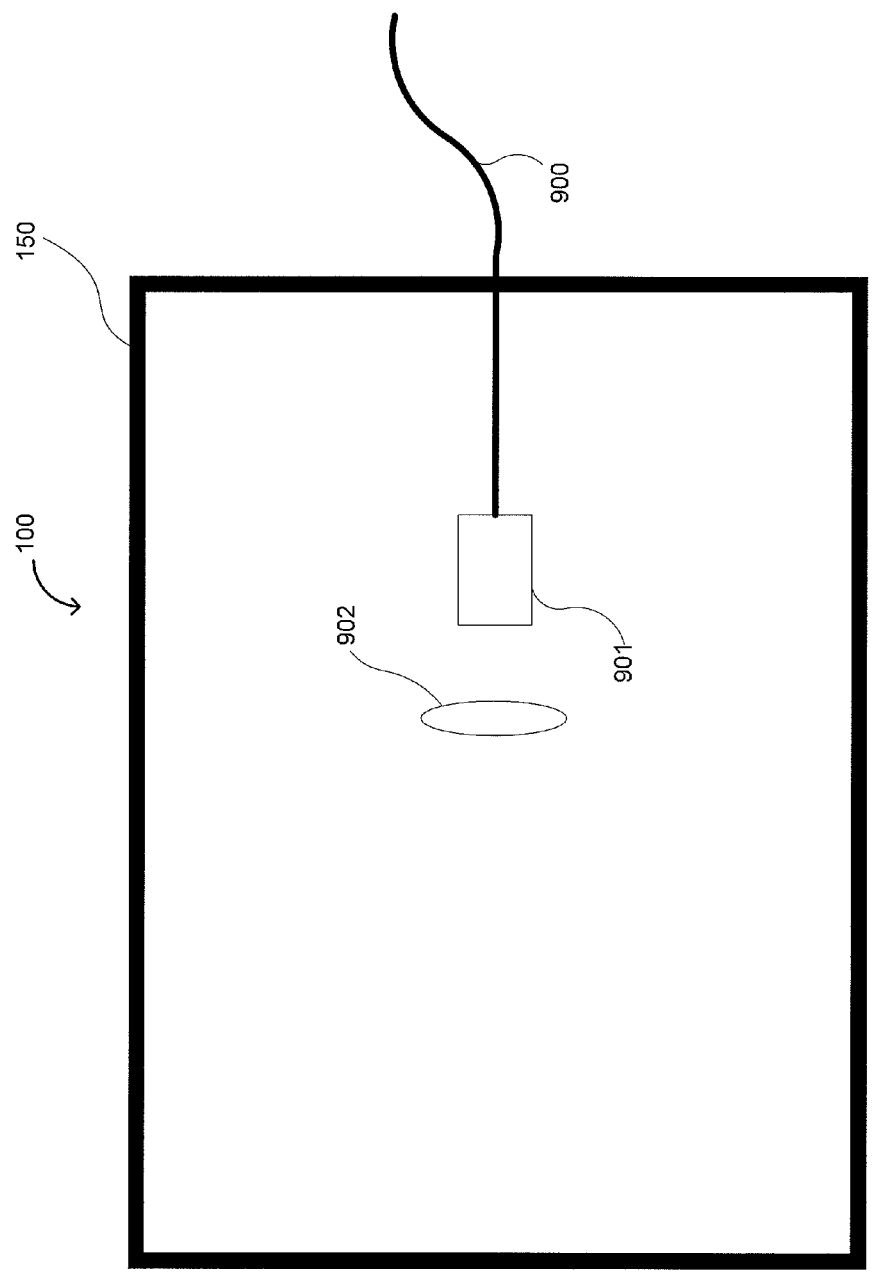
FIG. 9 depicts an example embodiment of a multi-laser system in which the target object comprises an optical fiber or waveguide.

FIG. 9 depicts an example embodiment of a multi-laser system in which the target object 1100 comprises an optical fiber or waveguide. An optional lens 902 may be used to couple the beams into the optical fiber 900. As shown in FIG. 9, the n laser beams may be combined, for example, by one of the embodiments for beam positioning and combining described above, or any combination of the embodiments described above and coupled into an optical fiber or waveguide. Both the coupling optics and fiber or waveguide may be located inside the temperature controlled enclosure and hard-mounted to the enclosure's temperature controlled base plate 901.

Figure 10:
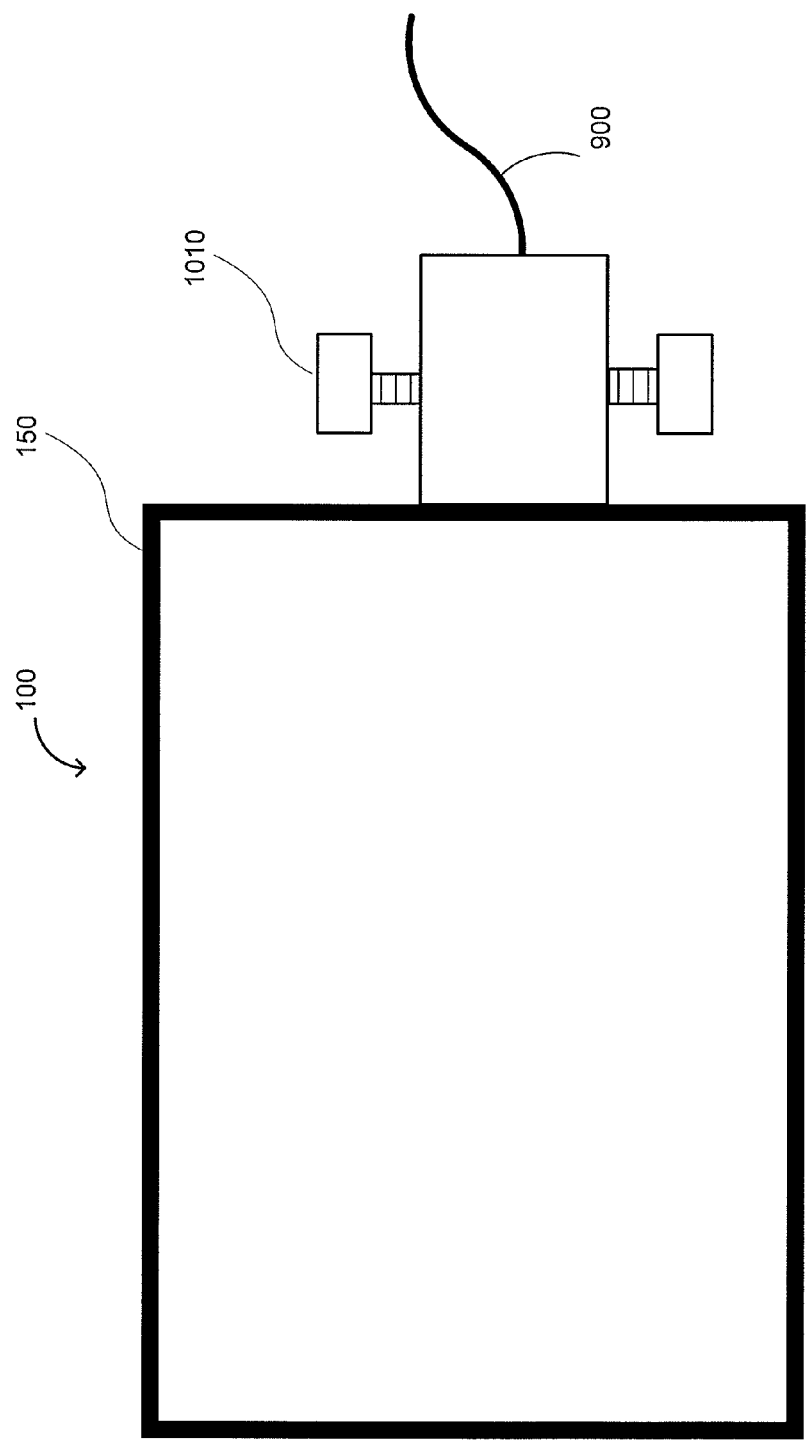
FIG. 10 depicts an example embodiment of a multi-laser system in which the target object comprises an adjuster mount.

FIG. 10 depicts an example embodiment of a multi-laser system in which the target object 1100 comprises an adjuster mount 1010. This adjuster mount may be configured to receive an optical fiber 900. Fiber optic coupling mounts are commercially available. In various embodiments, the fiber optic coupling mounts may comprise coupling optics mounted one focal length away from the optical fiber input with the optical axis of the coupling optics co-linear with a beam that would be emitted from the optical fiber. The coupling optics and optical fiber are mounted in a metal housing (e.g., a cylindrical housing) so that the alignment between the coupling optics and optical fiber input is maintained. This component may be a coupler/collimator assembly. In some embodiments, the mounts may comprise coupling optics and fiber in a metal housing. The coupler/collimator assembly is inserted into a positioning mount which is attached to the temperature controlled enclosure. For polarization maintaining fibers the coupler/collimator assembly and positioning mounts may be keyed so as to provide registration between the polarization axis of the laser beams and the polarization axis of the optical fiber. The positioning mount may be made of metal. The mount has mechanical adjusters that allow the pitch, yaw and lateral position of the coupler/collimator assembly to be moved relative to the input laser beams to optimize the amount of light coupled into the optical fiber. As shown in FIG. 10, the n laser beams may be combined, for example, by one of the embodiments for beam positioning and combining described above, or any combination of the embodiments described above and coupled into the adjustor mount or an optical element such as an optical fiber coupled to the adjuster mount. The optical fiber, coupling optics and coupling optimization hardware may be mounted at least partially on the outside of the temperature controlled enclosure.

Figure 11A:
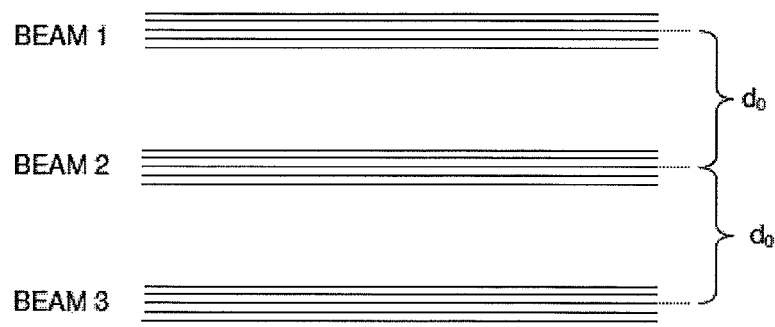
FIGS. 11A-11N depict example spatial arrangements of laser beams in multi-laser systems.
Figure 11B:
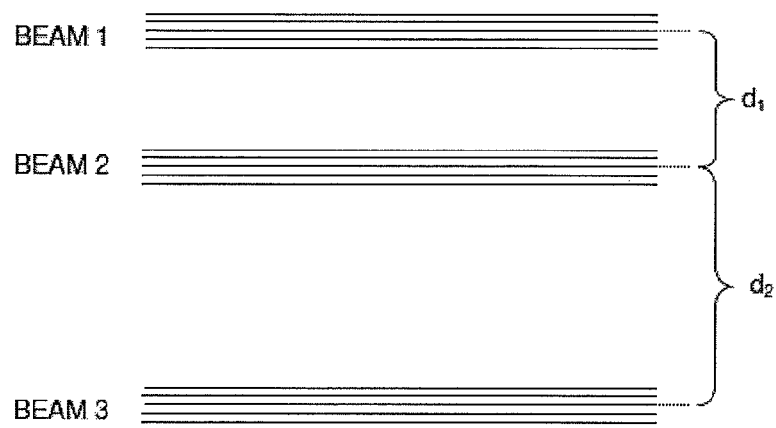
Figure 11C:
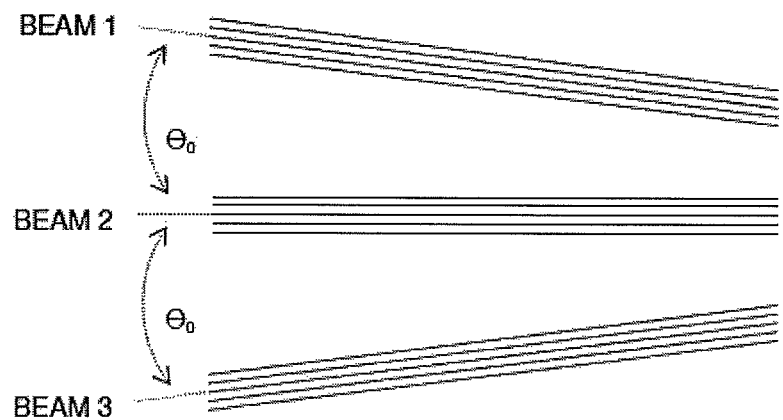
Figure 11D:
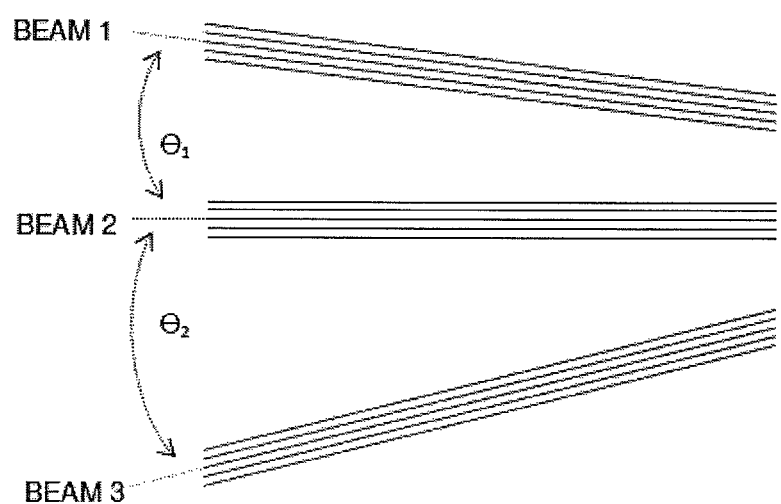
Figure 11E:
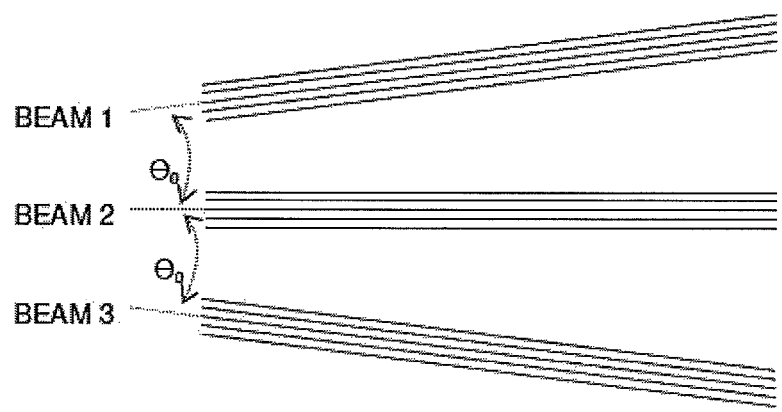
Figure 11F:
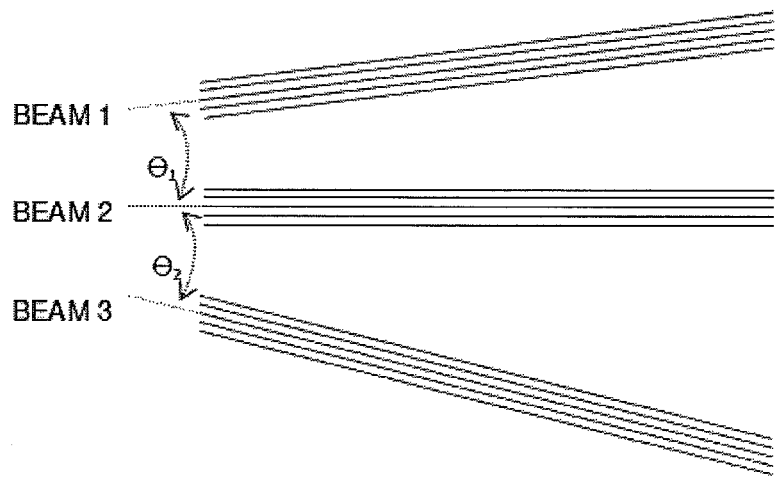
Figure 11G:
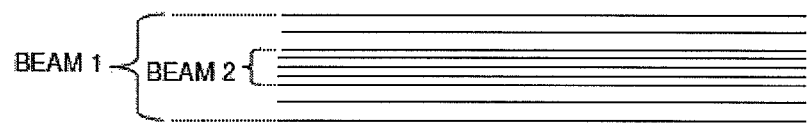
Figure 11H:
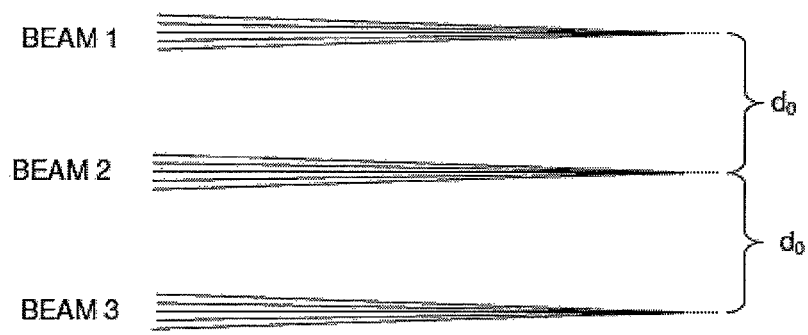
Figure 11I:
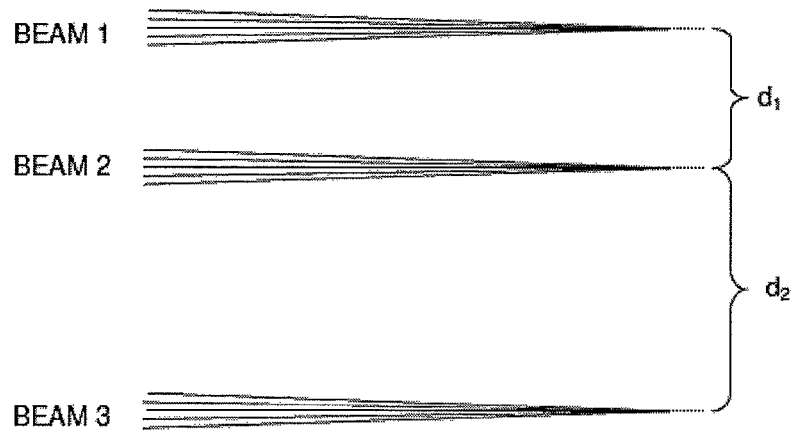
Figure 11J:
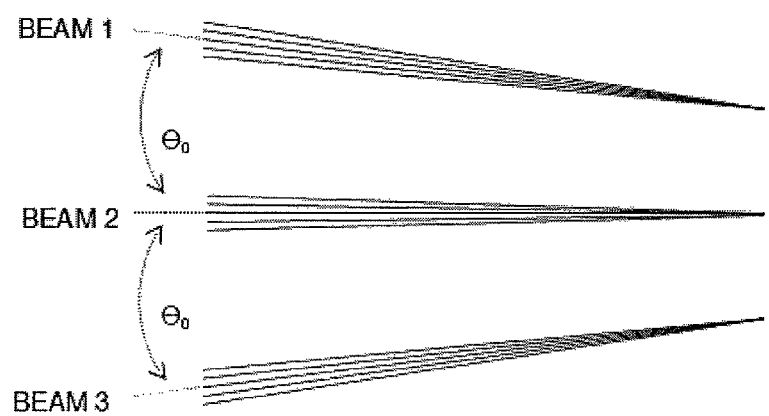
Figure 11K:
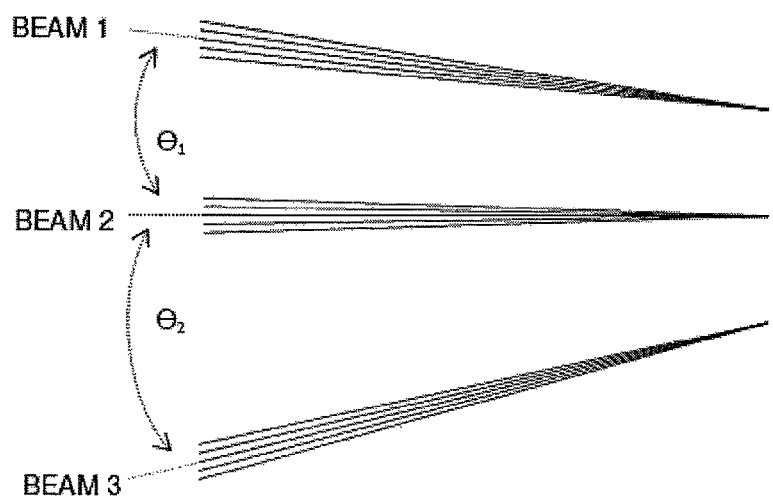
Figure 11L:
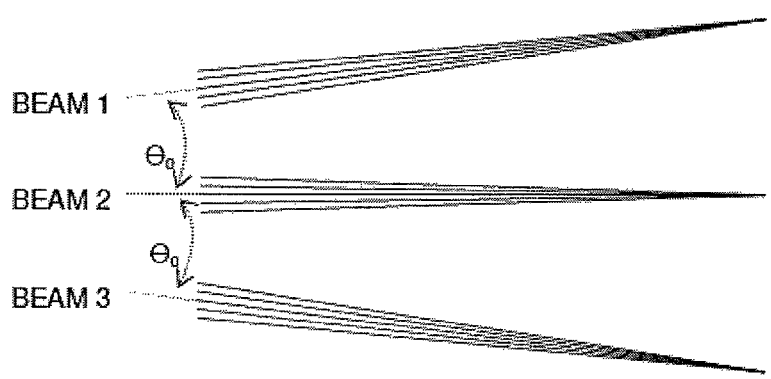
Figure 11M:
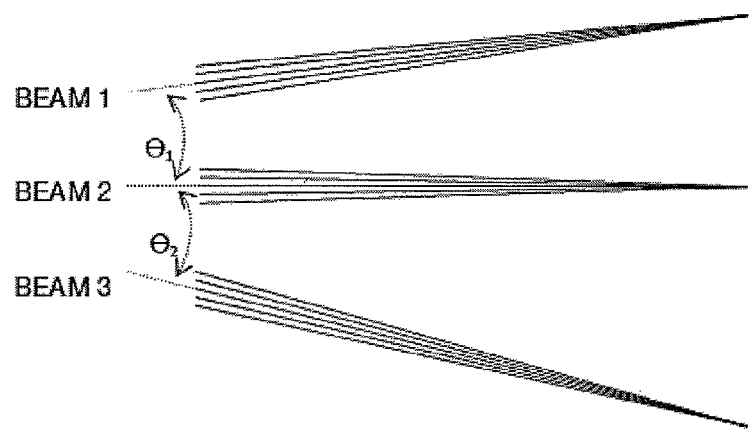
Figure 11N:
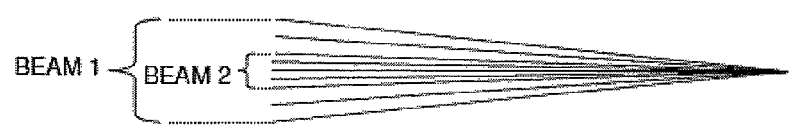

FIGS. 11A-11N depict example types and spatial arrangements of laser beams in multi-laser systems. The specific desired type and spatial arrangement of the laser beams may be application specific. The laser beams themselves may be collimated or focused. In some applications, however, it may be desirable to focus the laser beam in order to create small spot sizes at the target object and, hence, to increase power density or brightness on the target object. Accordingly, laser beams that are collimated or focused beams may be used. A plurality of collimated or a plurality of focused beams may be substantially co-linear to one another at the target object. The plurality of beams may alternatively be substantially parallel to one another but spaced apart from each other, or converging towards each other, or diverging away from one another at the target object. In some embodiments, the plurality of parallel beams may have identical beam separations (such as a substantially constant separation $d_0$) at the target object, or different beam separations (such as separations $d_1, d_2, \ldots$) at the target object. In some embodiments, the plurality of converging or diverging beams may have identical angular separations (such as a substantially constant separation $\theta_0$) at the target object, or different angular separations (such as separations $\theta_1, \theta_2, \ldots$) at the target object. In some embodiments, the angular separation may be less than about 5°.

Some example spatial arrangements of laser beams are depicted in FIGS. 11A-11N.

FIG. 11A depicts parallel collimated beams with identical beam separations, $d_0$.

FIG. 11B depicts parallel collimated beams with different beam separations, $d_1$ and $d_2$.

FIG. 11C depicts converging collimated beams with identical angular separations, $\theta_0$.

FIG. 11D depicts converging collimated beams with different angular separations, $\theta_1$ and $\theta_2$.

FIG. 11E depicts diverging collimated beams with identical angular separations, $\theta_0$.

FIG. 11F depicts diverging collimated beams with different angular separations, $\theta_1$ and $\theta_2$.

FIG. 11G depicts co-linear collimated beams.

FIG. 11H depicts parallel focused beams with identical beam separations, $d_0$.

FIG. 11I depicts parallel focused beams with different beam separations, $d_1$ and $d_2$.

FIG. 11J depicts converging focused beams with identical angular separations, $\theta_0$.

FIG. 11K depicts converging focused beams with different angular separations, $\theta_1$ and $\theta_2$.

FIG. 11L depicts diverging focused beams with identical angular separations, $\theta_0$.

FIG. 11M depicts diverging focused beams with different angular separations, $\theta_1$ and $\theta_2$.

FIG. 11N depicts co-linear focused beams.

Configurations other than those described herein are possible. The structures, devices, systems, and methods may include additional components, features, and steps and any of these components, features, and steps may be excluded and may or may not be replaced with others. The arrangements may be different. Reference throughout this specification to "some embodiments," "certain embodiments," or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

Although the inventions presented herein have been disclosed in the context of certain preferred embodiments and examples, it will be understood by those skilled in the art that the inventions extend beyond the specifically disclosed embodiments to other alternative embodiments and/or uses of the inventions and obvious modifications and equivalents thereof. Thus, it is intended that the scope of the inventions herein disclosed should not be limited by the particular embodiments described above.

What is claimed is:

1. A compact, thermally stable multi-laser system, comprising:
    a plurality of lasers outputting a plurality of respective laser beams;
    a plurality of beam adjusters configured to align said laser beams output from said plurality of lasers thereby outputting a plurality of adjusted laser beams;
    a beam positioning system configured to alter a position of the plurality of adjusted laser beams relative to one another, thereby outputting a plurality of positioned and adjusted laser beams;
    a thermally stable enclosure enclosing the plurality of lasers and the beam positioning system, the thermally stable enclosure substantially comprising a material having a thermal conductivity of at least 5 W/(m K), the thermally stable enclosure configured to maintain alignment of said laser beams output from the lasers over a range of ambient temperatures, wherein the plurality of positioned and adjusted laser beams are output as parallel laser beams to a target object located outside the enclosure; and
    a temperature controller configured to control the temperature of the thermally stable enclosure.

2. The system of claim 1, wherein the thermally stable enclosure is configured to thermally and mechanically couple to the target object.

3. The system of claim 1, wherein the temperature controller is configured to control the temperature of the target object.

4. The system of claim 1, wherein the target object comprises a flow cell.

5. The system of claim 2, wherein the thermally stable enclosure has a coefficient of thermal expansion and wherein a mounting mechanism for the target object has a thermal expansion coefficient that closely matches the coefficient of thermal expansion of the thermally stable enclosure.

6. The system of claim 1, wherein the target object comprises an optical fiber.

7. The system of claim 6, wherein the thermally stable enclosure encloses a portion of the optical fiber.

8. The system of claim 6, wherein the thermally stable enclosure has a coefficient of thermal expansion and wherein a mounting system for the optical fiber has a thermal expansion coefficient that closely matches the coefficient of thermal expansion of the thermally stable enclosure.

9. The system of claim 6, wherein said laser beams output from said lasers are co-linear at the optical fiber.

10. The system of claim 1, wherein the target object comprises an optical fiber in an adjuster mount configured to couple said laser beams output from said lasers into the optical fiber.

11. The system of claim 10, wherein the thermally stable enclosure has a coefficient of thermal expansion and wherein the adjuster mount has a thermal expansion coefficient that closely matches the coefficient of thermal expansion of the thermally stable enclosure.

12. The system of claim 10, wherein said laser beams output from the lasers are co-linear at the adjuster mount.

13. The system of claim 1, wherein relative heights of the lasers are configured to assist in relative positioning of said laser beams output from said lasers at the target object.

14. The system of claim 1, wherein said laser beams output from the lasers have centers separated by between about 100 µm and about 500 µm of one another at the target object.

15. The system of claim 1, wherein the thermally stable enclosure encloses beam focusing optics configured to focus said plurality of laser beams output by the lasers.

16. The system of claim 15, wherein the beam focusing optics includes an achromatic and anamorphic lens system configured to provide a laser beam with an elliptical shape at the target object.

17. The system of claim 15, wherein the beam focusing optics includes an achromatic spherical lens configured to provide a laser beam with an elliptical shape at the target object.

18. The system of claim 15, wherein the beam focusing optics includes an anamorphic prism system configured to provide a laser beam with an elliptical shape at the target object.

19. The system of claim 15, wherein the focused laser beams have respective focused spot sizes of between about 50 µm and about 150 µm in one direction.

20. The system of claim 15, wherein the focused laser beams have respective focused spot sizes of between 5 µm and 25 µm in a first direction.

21. The system of claim 1, wherein the plurality of lasers comprises at least one diode laser.

22. The system of claim 1, wherein the plurality of lasers comprises at least one solid-state laser.

23. The system of claim 1, wherein the plurality of lasers comprises at least one frequency-doubled laser.

24. The system of claim 1, wherein said plurality of laser beams output by the lasers comprises at least a first laser beam at a first wavelength, a second laser beam at a second wavelength different from the first wavelength, and a third laser beam at a third wavelength different from the first wavelength and the second wavelength.

25. The system of claim 1, wherein the beam positioning system comprises a plurality of wavelength selective mirrors configured to reflect at least one wavelength and to transmit at least one other wavelength.

26. The system of claim 1, wherein the beam positioning system comprises one or more prisms with wavelength selective surfaces configured to reflect at least one wavelength and to transmit at least one other wavelength.

27. The system of claim 1, further comprising flexure mounts supporting the beam positioning system.

28. The system of claim 1, wherein the plurality of beam adjusters is configured to align said laser beams output from said plurality of lasers prior to entering the beam positioning system.

29. The system of claim 1, wherein at least one of yaw, pitch, and separation between at least one of said beam adjusters is adjustable.

30. The system of claim 1, wherein said plurality of beam adjusters comprises a plurality of plane parallel plates configured to shift the laser beams in at least one direction.

31. The system of claim 30, wherein at least one of said plane parallel plates is adjustable.

32. The system of claim 1, further comprising an automatic power control module in communication with each said laser.

33. The system of claim 1, wherein at least one of a polarization rotator or a waveplate is used to rotate a laser beam polarization of at least one of said laser beams to obtain a laser beam polarization orientation that enhances system performance.

34. The system of claim 1, wherein the temperature controller is configured to hold a temperature within the thermally stable enclosure within about ±3° C. of a target temperature.

35. The system of claim 34, wherein the target temperature is between about 10° C. and about 50° C.

36. The system of claim 34, wherein the thermally stable enclosure is configured to thermally couple to the target object.

37. The system of claim 1, wherein the thermally stable enclosure is hermetically sealed.

38. The system of claim 1, wherein the temperature controller comprises a thermal electric cooler, a temperature sensor, and control electronics.

39. The system of claim 1, wherein the range of ambient temperatures is between about 10° C. and about 55° C.

40. The system of claim 1, wherein the thermally stable enclosure has a volume of 216 in$^3$ or less.

41. The system of claim 1, wherein the target object comprises a light pipe.

42. The system of claim 1, wherein the target object comprises a waveguide.

43. The system of claim 1, wherein the target object comprises a lab on a chip.

44. The system of claim 1, further comprising glue-block mounts supporting the beam positioning system.

45. A method of adjusting a plurality of laser beams, the method comprising:
   using a plurality of beam adjusters to redirect the plurality of laser beams by changing beam angles of the plurality of laser beams thereby outputting a plurality of adjusted laser beams;
   using a plurality of plane parallel plates to change the lateral position of the plurality of adjusted laser beams, thereby outputting a plurality of positioned and adjusted laser beams; and
   using a beam positioning system to alter a position of the plurality of positioned and adjusted laser beams closer together, thereby outputting parallel laser beams.

46. The system of claim 45, wherein the beam positioning system comprises a plurality of wavelength selective mirrors.

47. A compact, thermally stable laser system, comprising:
   a laser outputting a laser beam;

a beam adjuster configured to alter a position of the laser beam, wherein the beam adjuster comprises a rotatable Risley prism pair configured to change the angle of said laser beam output from said laser, thereby outputting an adjusted laser beam;

a thermally stable enclosure enclosing the laser and the beam adjuster, the thermally stable enclosure substantially comprising a material having a thermal conductivity of at least 5 W/(m K), the thermally stable enclosure configured to maintain alignment of the adjusted laser beam to a target object located outside the enclosure over a range of ambient temperatures; and a temperature controller configured to control the temperature of the thermally stable enclosure.

48. The system of claim 20, wherein the focused laser beams have respective focused spot sizes of between about 50 μm and about 150 μm in a second direction orthogonal to the first direction.

49. The system of claim 1, wherein the laser beams are collimated at the target object, wherein the laser beams are parallel at the target object, and wherein the laser beams have centers separated by substantially equal separations at the target object.

50. The system of claim 1, wherein the laser beams are collimated at the target object, wherein the laser beams are parallel at the target object, and wherein the laser beams have centers separated by different separations at the target object.

51. The system of claim 1, wherein the parallel laser beams are focused at the target object, and wherein the laser beams have centers seperated by substantially equal separations at the target object.

52. The system of claim 1, wherein said plurality of beam adjusters comprises a plurality of rotatable Risley prism pairs configured to change the angle of said laser beams output from said plurality of lasers.

53. The method of claim 45, wherein the plurality of laser beams are output from a plurality of light sources.

54. The method of claim 45, wherein the method comprises using said plane parallel plates to change the lateral position of the plurality of adjusted laser beams after using said plurality of beam adjusters to redirect the plurality of laser beams by changing the beam angles of the plurality of laser beams, and comprises using said beam positioning system to reposition the plurality of positioned and adjusted laser beams closer together after using said plane parallel plates to change the lateral position of the plurality of adjusted laser beams.

55. The system of claim 45, wherein the plurality of beam adjusters comprises a plurality of rotatable Risley prism pairs.

56. A compact, thermally stable multi-laser system, comprising:

a plurality of lasers outputting a plurality of respective laser beams;

a plurality of beam adjusters configured to align said laser beams output from said plurality of lasers thereby outputting a plurality of adjusted laser beams;

a beam positioning system configured to alter a position of the plurality of adjusted laser beams relative to one another, thereby outputting a plurality of positioned and adjusted laser beams;

a thermally stable enclosure enclosing the plurality of lasers and the beam positioning system, the thermally stable enclosure substantially comprising a material having a thermal conductivity of at least 5 W/(m K), the thermally stable enclosure configured to maintain alignment of said laser beams output from the lasers over a range of ambient temperatures, wherein the plurality of positioned and adjusted laser beams are output as separate laser beams to a target object located outside the enclosure; and a temperature controller configured to control the temperature of the thermally stable enclosure.

57. The system of claim 1, wherein the laser beams are focused at the target object, wherein the laser beams are parallel at the target object, and wherein the laser beams have centers seperated by different separations at the target object.

* * * * *

UNITED STATES PATENT AND TRADEMARK OFFICE
CERTIFICATE OF CORRECTION

| | |
|---|---|
| PATENT NO. | : 9,014,224 B2 |
| APPLICATION NO. | : 12/940004 |
| DATED | : April 21, 2015 |
| INVENTOR(S) | : John O'Shaughnessy |

It is certified that error appears in the above-identified patent and that said Letters Patent is hereby corrected as shown below:

In the Specification

At column 10, line 45, please delete "minors" and insert --mirrors--, therefor.

At column 10, line 48, please delete "minors" and insert --mirrors--, therefor.

At column 12, line 56, please delete "ore" and insert --or--, therefor.

At column 13, line 49, please delete "ore" and insert --or--, therefor.

In the Claims

At column 24, line 42, Claim 40, please delete "216 in$^3$or" and insert --216 in$^3$ or--, therefor.

At column 25, line 30, Claim 51, please delete "seperated" and insert --separated--, therefor.

At column 26, line 38, Claim 57, please delete "seperated" and insert --separated--, therefor.

Signed and Sealed this
Fifth Day of April, 2016

Michelle K. Lee
*Director of the United States Patent and Trademark Office*